(12) United States Patent
Hodgkinson et al.

(10) Patent No.: US 10,420,661 B2
(45) Date of Patent: Sep. 24, 2019

(54) STENTS AND STENT DEPLOYMENT DEVICES

(71) Applicant: Covidien LP, Mansfield, MA (US)

(72) Inventors: Gerald Hodgkinson, Guilford, CT (US); David Racenet, Killingworth, CT (US); Stanislaw Kostrzewski, Newtown, CT (US); Stanislaw Marczyk, Stratford, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 60 days.

(21) Appl. No.: 15/372,041

(22) Filed: Dec. 7, 2016

(65) Prior Publication Data

US 2017/0172774 A1 Jun. 22, 2017

Related U.S. Application Data

(60) Provisional application No. 62/268,692, filed on Dec. 17, 2015.

(51) Int. Cl.
*A61F 2/95* (2013.01)
*A61F 2/04* (2013.01)
(Continued)

(52) U.S. Cl.
CPC .................. *A61F 2/95* (2013.01); *A61F 2/04* (2013.01); *A61F 2/07* (2013.01); *A61F 2/82* (2013.01);
(Continued)

(58) Field of Classification Search
CPC . A61B 50/20; A61B 50/30; A61F 2/95; A61F 2002/9505; A61F 2002/9511;
(Continued)

(56) References Cited

U.S. PATENT DOCUMENTS

| 5,480,423 A | 1/1996 | Ravenscroft et al. |
| 5,575,818 A | 11/1996 | Pinchuk |

(Continued)

FOREIGN PATENT DOCUMENTS

WO 2006005082 A2 1/2006

OTHER PUBLICATIONS

European Search Report dated Jun. 6, 2017, issued in EP Application No. 16204716.

*Primary Examiner* — Seema Mathew

(57) ABSTRACT

A method of deploying a stent includes receiving a delivery system loaded with a stent and securing the stent in a compressed arrangement by a stent holding assembly including first and second holders having a first protective cover disposed at one end for enclosing a first fastening assembly and a second protective cover disposed at one end of the second holder for enclosing a second fastening assembly, respectively, the stent coupled to the first and second holders members by the first and second fastening assemblies, respectively. The method further includes delivering the stent in an axially expanded and a radially compressed arrangement to an implantation site, retracting the first and second protective covers to expose the first and second fastening assemblies, and actuating the first and second fastening assemblies such that the stent radially expands to engage an inner wall of a lumen.

9 Claims, 33 Drawing Sheets

(51) Int. Cl.
  *A61F 2/915* (2013.01)
  *A61F 2/848* (2013.01)
  *A61F 2/92* (2013.01)
  *A61F 2/07* (2013.01)
  *A61F 2/82* (2013.01)

(52) U.S. Cl.
  CPC .............. *A61F 2/848* (2013.01); *A61F 2/915* (2013.01); *A61F 2/92* (2013.01); *A61F 2002/041* (2013.01); *A61F 2002/044* (2013.01); *A61F 2002/045* (2013.01); *A61F 2002/9517* (2013.01)

(58) Field of Classification Search
  CPC ...... A61F 2002/9517; A61F 2002/9534; A61F 2220/0075; A61F 2002/9522; A61F 2002/91591
  See application file for complete search history.

(56) References Cited

U.S. PATENT DOCUMENTS

| | | | |
|---|---|---|---|
| 5,645,559 A | 7/1997 | Hachtman et al. | |
| 5,681,346 A | 10/1997 | Orth et al. | |
| 5,800,526 A | 9/1998 | Anderson et al. | |
| 5,817,102 A | 10/1998 | Johnson et al. | |
| 6,562,063 B1* | 5/2003 | Euteneuer | A61F 2/95 606/198 |
| 6,565,595 B1* | 5/2003 | DiCaprio | A61F 2/958 623/1.11 |
| 6,576,005 B1 | 6/2003 | Geitz | |
| 6,676,692 B2* | 1/2004 | Rabkin | A61F 2/95 604/104 |
| 7,967,138 B2* | 6/2011 | Ryan | A61F 2/0095 206/370 |
| 8,372,134 B2 | 2/2013 | Schlick et al. | |
| 8,372,142 B2 | 2/2013 | Majercak et al. | |
| 8,753,407 B2 | 6/2014 | Nguyen | |
| 9,119,717 B2* | 9/2015 | Wang | A61F 2/2436 |
| 9,370,422 B2* | 6/2016 | Wang | A61F 2/2436 |
| 9,387,074 B2* | 7/2016 | Costello | A61F 2/95 |
| 2005/0049667 A1* | 3/2005 | Arbefeuille | A61F 2/07 623/1.11 |
| 2005/0085848 A1* | 4/2005 | Johnson | A61F 2/013 606/200 |
| 2006/0095116 A1* | 5/2006 | Bolduc | A61B 17/064 623/1.16 |
| 2007/0213813 A1 | 9/2007 | Von Segesser et al. | |
| 2007/0239252 A1* | 10/2007 | Hopkins | A61F 2/95 623/1.11 |
| 2007/0293930 A1* | 12/2007 | Wang | A61F 2/91 623/1.11 |
| 2008/0132990 A1 | 6/2008 | Richardson | |
| 2009/0192585 A1* | 7/2009 | Bloom | A61F 2/2412 623/1.11 |
| 2009/0270967 A1 | 10/2009 | Fleming, III et al. | |
| 2009/0287290 A1* | 11/2009 | Macaulay | A61F 2/2412 623/1.11 |
| 2010/0152834 A1* | 6/2010 | Hannes | A61F 2/90 623/1.15 |
| 2010/0161032 A1* | 6/2010 | Avellanet | A61L 31/005 623/1.15 |
| 2010/0274187 A1* | 10/2010 | Argentine | A61F 2/95 604/96.01 |
| 2010/0292780 A1* | 11/2010 | Straubinger | A61F 2/2427 623/1.23 |
| 2011/0184507 A1 | 7/2011 | Fischer, Jr. et al. | |
| 2011/0264186 A1 | 10/2011 | Berglung et al. | |
| 2011/0301703 A1* | 12/2011 | Glazier | A61F 2/2418 623/2.17 |
| 2011/0307049 A1* | 12/2011 | Kao | A61F 2/966 623/1.11 |
| 2012/0041533 A1 | 2/2012 | Bertolino et al. | |
| 2012/0165916 A1* | 6/2012 | Jordan | A61F 2/95 623/1.11 |
| 2012/0303132 A1 | 11/2012 | Kim et al. | |
| 2014/0094929 A1* | 4/2014 | Shin | A61F 2/95 623/23.66 |
| 2017/0216068 A1* | 8/2017 | Dwyer | A61F 2/958 |

* cited by examiner

STENTS AND STENT DEPLOYMENT DEVICES

CROSS-REFERENCE TO RELATED APPLICATIONS

This application claims the benefit of and priority to U.S. Provisional Patent Application No. 62/268,692 filed Dec. 17, 2015, the entire disclosure of which is incorporated by reference herein.

TECHNICAL FIELD

The present disclosure relates to medical instrumentation. More particularly, the present disclosure relates to stents and stent deployment devices.

BACKGROUND OF RELATED ART

A stent is an elongated device used to support a luminal wall. Together a stent, along with a graft cover or liner, provide an unobstructed conduit for fluid flow in the area of a stenosis. Such a stent-graft would typically have a tubular graft layer covering, or lining, the inside or outside of the stent (or both), thus providing a fluid conduit to bypass a stenosis or otherwise diseased body passageway.

Various types of stent architectures are known in the art, including many designs comprising a filament or number of filaments, such as a wire or wires, wound or braided into a particular configuration. Included among these wire stent configurations are braided stents. Braided stents tend to be very flexible, having the ability to be placed in tortuous anatomy and still maintain patency. The flexibility of braided stents makes them particularly well-suited for use in intraluminal delivery where the lumen of the vessel becomes contorted and irregular both before and after placement of the stent.

The most common use of stents and stent-grafts is in the vascular system, in which stents and stent-grafts having a first small diameter compressed configuration may be introduced into a body lumen at a point remote from a site in that lumen in need of repair and then transported through that lumen, typically through a catheter, to that site. Once the site in need of repair is reached, the stent or stent-graft is either expanded or allowed to expand to a second, expanded configuration to provide an open passageway through that site.

Many of these braided stents, however, are either too rigid such that intraluminal delivery and placement becomes difficult or too flexible (at the cost of reducing radial strength) such that radial expansion forces exhibited at the site of treatment are insufficient to adequately maintain an open passageway through the site. Moreover, by increasing the radial strength of a stent, one typically reduces flexibility, because the stent is more rigid. Likewise, by increasing flexibility, radial strength is often sacrificed.

In the field of gastrointestinal surgery, resection of diseased tissue and maintenance of gastrointestinal continuity upon re-anastomosis can result in leaks. There are several factors contributing to a risk of a leak. These are, for example, the location of the anastomosis, overall health of re-connected tissue, previous treatments (e.g., radiation, chemotherapy, etc.), pre-existing condition (e.g., diabetes), tension the connection is undergoing during bowel movement, possible infection from the intestinal content, and quality of surgical technique.

It is contemplated that a stent and stent delivery system could be deployed to protect the anastomosis from bowel contents during the healing phase to reduce the risk of anastomotic leaks.

SUMMARY

The present disclosure relates to a stent deployment system. The stent deployment system includes a handle body, a stent holding assembly including a first holder and a second holder, the stent holding assembly connected to the handle body, wherein the first holder is connected to the second holder via a shaft defining a longitudinal axis such that the first and second holders are substantially aligned with the longitudinal axis, a stent having a proximal end and a distal end, the stent secured to the stent holding assembly such that at least a portion of the stent holding assembly is confined within the stent, a first protective cover disposed at one end of the first holder, the first protective cover configured to enclose a first fastening assembly, and a second protective cover disposed at one end of the second holder, the second protective cover configured to enclose a second fastening assembly.

In disclosed embodiments, each of the first and second fastening assemblies includes a plurality of anchors mounted on distal ends of extensions, the extensions separated from each other by gaps.

In disclosed embodiments, the first and second fastening assemblies are exposed upon removal of the first and second protective covers, respectively.

In disclosed embodiments, the first holder includes a first sleeve and the second holder includes a second sleeve, the first and second sleeves removed before deployment of the first and second fastening assemblies.

In disclosed embodiments, upon removal of the first and second sleeves, the extensions of each of the first and second fastening assemblies are actuated to extend away from the first and second holders to engage a lumen.

In disclosed embodiments, the stent is positioned within the lumen in an axially expanded configuration.

In disclosed embodiments, when the first and second fastening assemblies are actuated to extend away from the first and second holders, the stent secured thereon deforms to a radially expanded configuration.

In disclosed embodiments, the first and second holders are independently driven.

In disclosed embodiments, each of the first and second holders is a substantially cylindrical enclosure, where the respective first and second fastening assemblies are circumferentially positioned therein.

In disclosed embodiments, each of the first and second fastening assemblies is a coiled anchoring ring having a plurality of projections disposed on an outer surface thereof. The coiled anchoring ring of each of the first and second fastening assemblies is mounted around a balloon.

The present disclosure relates to a method of deploying a stent to an implantation site. The method includes the steps of receiving a delivery system loaded with a stent and securing the stent in a compressed arrangement by a stent holding assembly including a first holder and a second holder, the first holder having a first protective cover disposed at one end for enclosing a first fastening assembly therein and a second protective cover disposed at one end of the second holder member for enclosing a second fastening assembly therein, the stent coupled to the first and second holders by the first and second fastening assemblies, respectively. The method further includes the steps of delivering the stent in an axially expanded and a radially compressed arrangement through a bodily lumen and to the implantation site via the delivery system, retracting the first and second protective covers to expose the first and second fastening assemblies, and actuating the first and second fastening assemblies to extend away from the first and second holders, respectively, such that the stent radially expands to engage an inner wall of the bodily lumen, while axially contracting to remove tension from the anastomosis.

DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
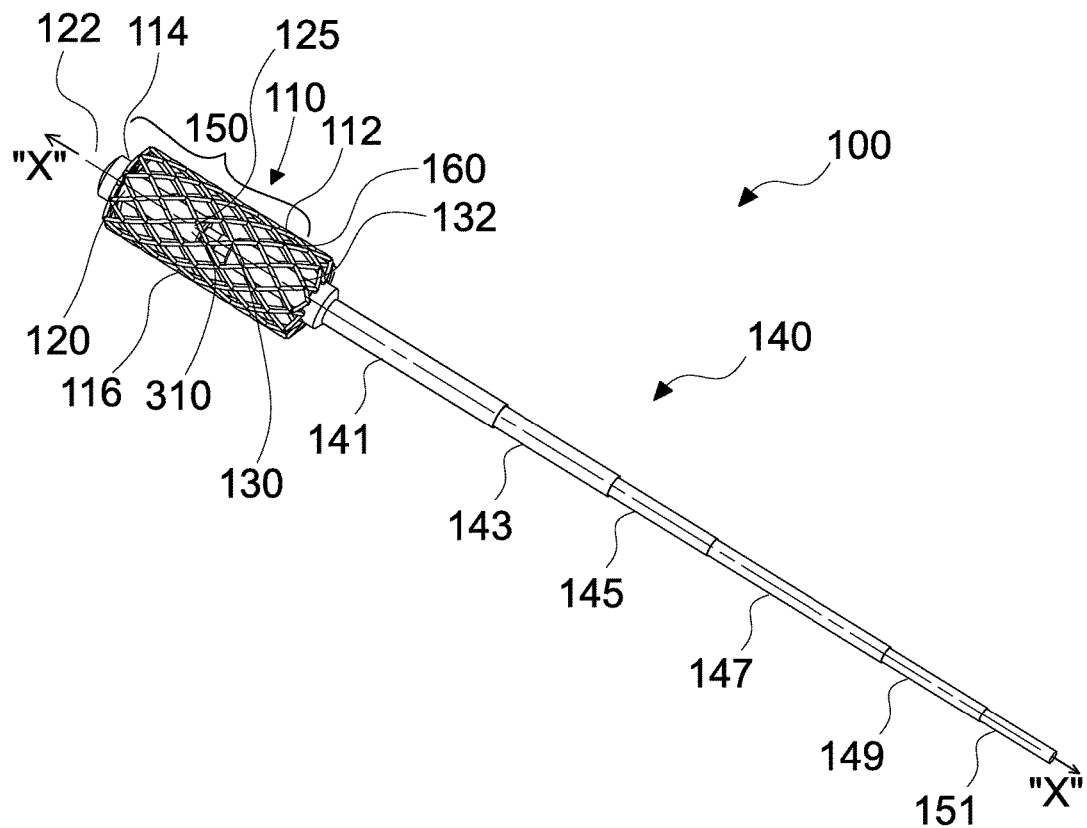
FIG. 1 illustrates a perspective view of a colonic/esophageal stent deployment device with a stent in a first state, in accordance with an embodiment of the present disclosure.

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for disclosing how to employ aspects of the present disclosure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user. In addition, the term "endoscopic" is used generally to refer to endoscopic, laparoscopic, or arthroscopic apparatus or procedures as well as any other surgical apparatus or procedure that is configured to extend or be performed through a small incision or a cannula inserted into a patient's body. Finally, the term "clinician" is used generally to refer to medical personnel including doctors, nurses, and support personnel.

Reference will now be made in detail to embodiments of the present disclosure. While certain exemplary embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

FIG. 1 illustrates a perspective view of a colonic/esophageal stent deployment device 100 with a stent 110 in a first state, in accordance with an embodiment of the present disclosure.

The stent deployment device 100 includes a stent holding assembly 150 connected to a handle body 140. The stent holding assembly 150 includes a first holder 120 and a second holder 130. The first holder 120 is connected to the second holder 130 at a connection point 125 by a shaft 310 defining a longitudinal axis "X." The first and second holders 120, 130 are substantially aligned with the longitudinal axis "X." The first and second holders 120, 130 may be independently driven stent holders.

Figure 5:
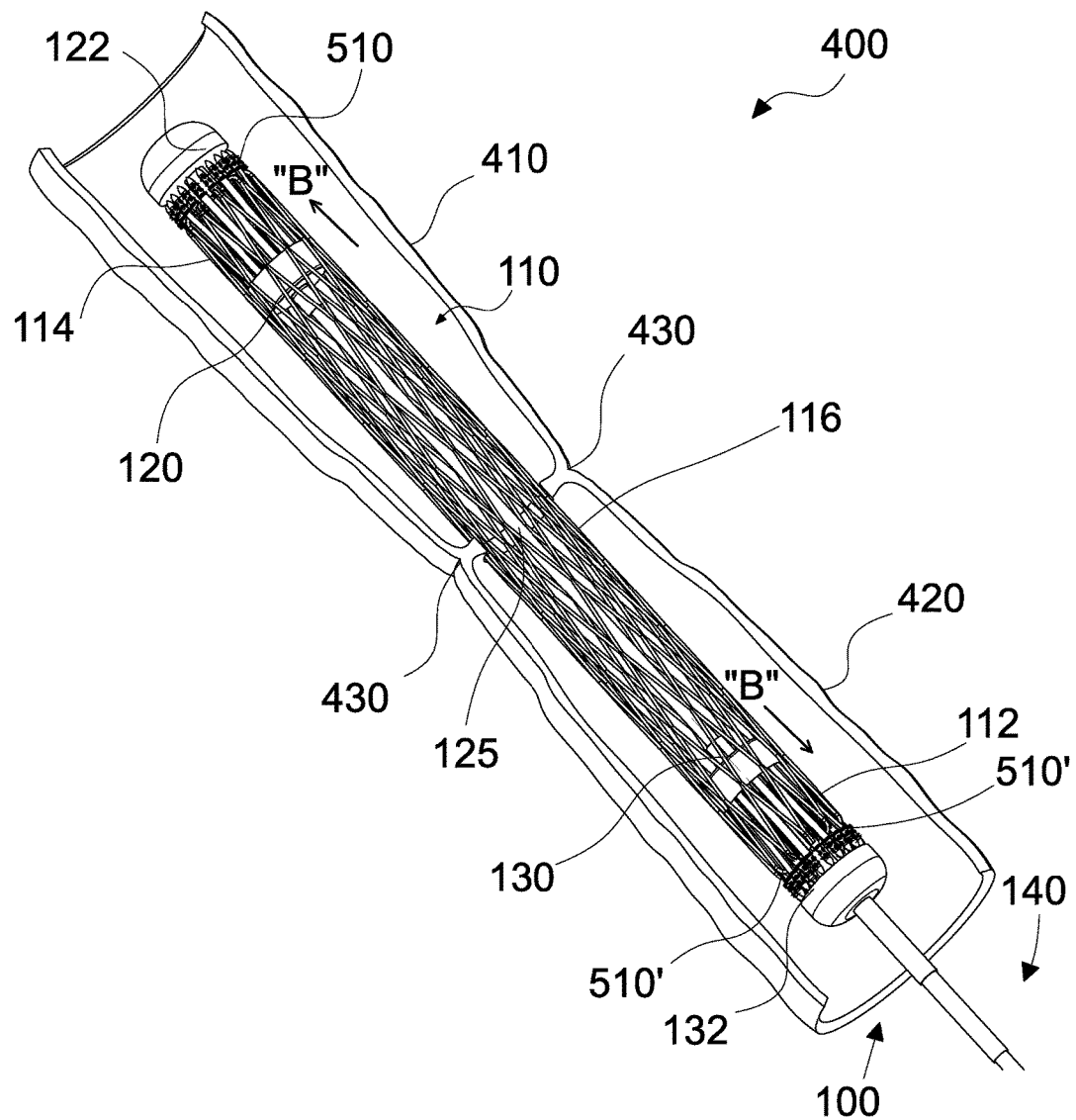
FIG. 5 illustrates the first and second protective covers of the stent of FIG. 3 removed in order to commence deployment of the stent within the lumen, in accordance with an embodiment of the present disclosure.
Figure 8:
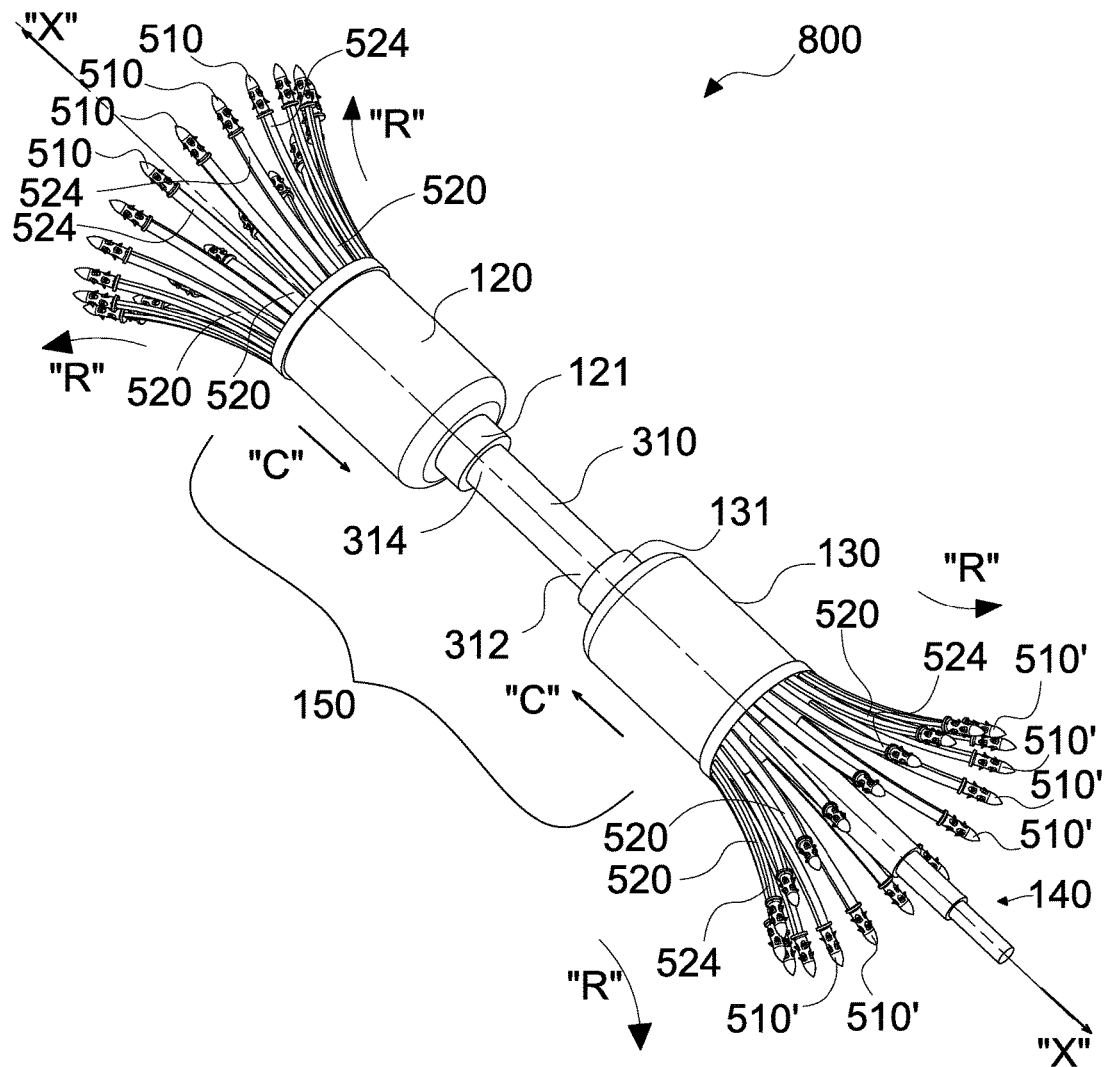
FIG. 8 illustrates radial deployment of the anchors of the stent holders, in accordance with an embodiment of the present disclosure.

The handle body 140 is formed as a telescoping body having a first telescoping section 141, a second telescoping section 143, a third telescoping section 145, a fourth telescoping section 147, a fifth telescoping section 149, and a sixth telescoping section 151. For example, the third telescoping section 145 may be configured to move the second holder 130 and the fourth telescoping section 147 may be configured to move the first holder 120. In this way, the third telescoping section 145 is manipulated to release the plurality of anchors 510' from the second holder 130 and the fourth telescoping section 149 is manipulated to release the plurality of anchors 510 from the first holder 120 (FIGS. 5 and 8).

Figure 4:
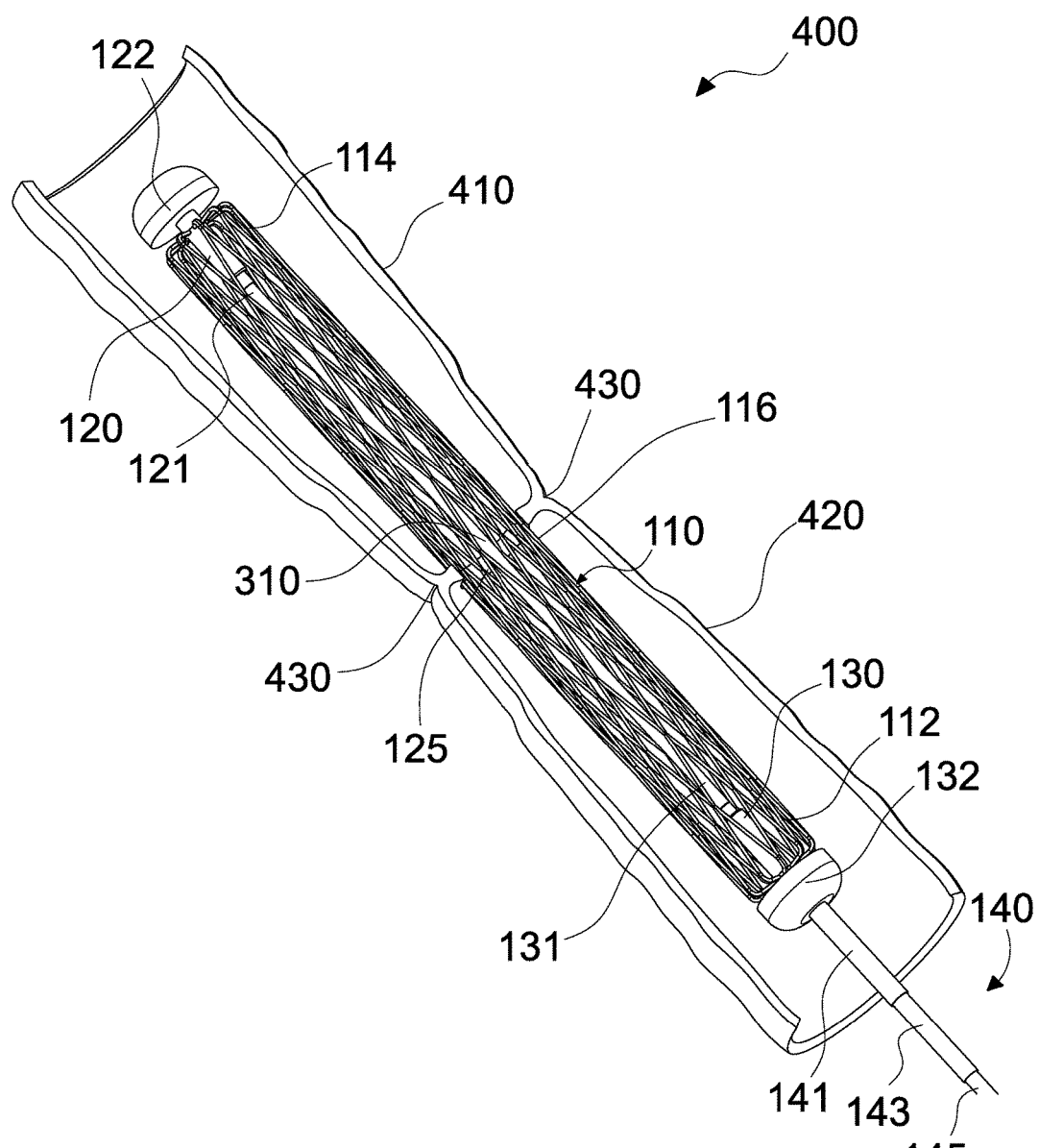
FIG. 4 illustrates the stent of FIG. 3 positioned within a lumen, in accordance with an embodiment of the present disclosure.

In one instance, the first telescoping section 141 may be configured to separate the protective covers 122, 132 from the first and second holders 120, 130. The fifth telescoping section 149 may be configured to remove the first and second holders 120, 130 from a lumen 400 after placement of the stent 110 in the lumen 400 (FIG. 4). The sixth telescoping section 151 may be configured to remove the protective covers 122, 132 from the lumen 400 after placement of the stent 110 in the lumen 400. Of course, one skilled in the art may contemplate using any of the first, second, third, fourth, fifth, and sixth telescoping sections 141, 143, 145, 147, 149, 151 for any suitable purpose. For example, such telescoping sections may be used to separate any components from other components or may be used to remove any components from the surgical site (e.g., placement of stent 110 within lumen 400).

The stent holding assembly 150 holds a stent 110 such that that stent holding assembly 150 is confined within the stent 110. The stent 110 is held in place by a fastening assembly 510 at one end and a fastening assembly 510' at the other end. Each fastening assembly 510, 510' includes a plurality of anchors for securing the stent 110 to the lumen 400, as will be described below in detail with reference to FIG. 4.

Thus, the stent 110 encircles the stent holding assembly 150. The stent 110 may have a first diameter. The first and second holders 120, 130 may have a second diameter. The first diameter is greater than the second diameter. The stent 110 has a proximal end 112 and a distal end 114. The stent 110 also has a central region 116. Stent 110 includes a generally cylindrical configuration and may include any suitable diameter or length depending on the size of the area of interest or the procedure being performed. Stent 110 is constructed of any suitable biocompatible material and, in some embodiments, may be formed from a bio-absorbable material. Stent 110 is resilient and is configured to compress or expand due to external stimuli.

A channel 160 is defined through stent 110 and has a diameter that is greater than the diameter of the first and second holders 120, 130, while the stent 110 is positioned or secured in lumen 400 (FIG. 4) to treat tissue and, ultimately dissolve or be retrieved at a later time. Stent 110 may be constructed from polymers, degradable polymers, suitable resilient metals, composites, or the like. In this manner, it is contemplated that stent 110 may be formed from a homogeneous construction or a heterogeneous construction (i.e., a combination of metallic and non-metallic bio-absorbable materials).

A first protective cover 122 is disposed at one end of the first holder 120, whereas a second protective cover 132 is disposed at one end of the second holder 130. The first and second protective covers 122, 132 are in opposed relation to each other and coaxial with longitudinal axis "X." The first protective cover 122 encloses a first fastening assembly 510 and the second protective cover 132 encloses a second fastening assembly 510' (FIG. 5). Each of the first and second fastening assemblies 510, 510' includes a plurality of anchors, as will be described below in detail. The first and second protective covers 122, 132 have tapered ends allowing stent deployment device 100 to be inserted atraumatically into a body lumen when the stent deployment device 100 is inserted and manipulated with lumen 400 (FIG. 4). The first protective cover 122 engages and secures the plurality of anchors 510 therein, whereas the second protective cover 132 engages and protects the plurality of anchors 510'. Thus, the proximal and distal ends 112, 114 of the stent 110 extend into the first and second protective covers 122, 132. How the proximal and distal ends 112, 114 of the stent 110 are held therein is described below.

Figure 2:
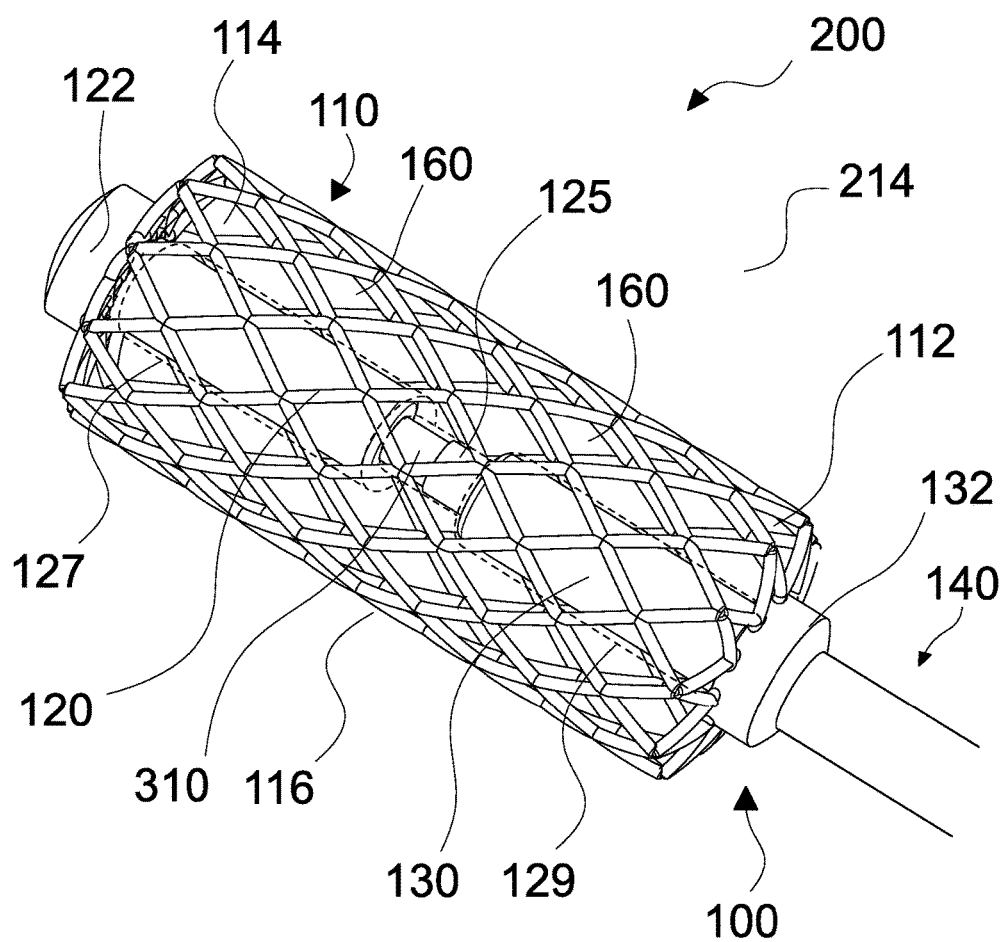
FIG. 2 illustrates an enlarged view of the distal end of the stent deployment device of FIG. 1 depicting the stent holders holding the stent, in accordance with an embodiment of the present disclosure.

FIG. 2 illustrates an enlarged view 200 of the distal end 214 of the stent deployment device 100 of FIG. 1 depicting the first and second holders 120, 130 holding the stent 110, in accordance with an embodiment of the present disclosure.

The stent 110 is shown in a first or uncompressed state. The stent 110 has a substantially cylindrical shape in the first state. The proximal end 112 of the stent 110 is attached to the plurality of fasteners 510' positioned within the second holder 130, whereas the distal end 114 of the stent 110 is attached to the plurality of fasteners 510 positioned within the first holder 120. Thus, the proximal and distal ends 112, 114 of the stent 110 are attached directly to the plurality of fasteners 510, 510' positioned within respective holders 130, 120. The plurality of fasteners 510, 510' are each attached to extensions 520, as described below in detail with respect to FIG. 6. In this way, the stent 110 bends inwardly at the proximal and distal ends 112, 114 to be accommodated by the stent holding assembly 150 in a first state.

The first and second holders 120, 130 are shown fully confined within the stent 110. The first and second holders 120, 130 are thus fully encompassed within the stent 110. The stent 110 does not contact the first and second holders 120, 130. However, the proximal and distal ends 112, 114 of the stent 110 contact an inner surface of the first and second holders 120, 130, respectively. Moreover, the first and second holders 120, 130 appear to be suspended within the stent 110. Therefore, in the first state, the stent 110 does not contact the first and second holders 120, 130 and a circumferential channel 160 is defined through the stent holding assembly 150. The stent 110 extends the length of both the first and second holders 120, 130.

The first holder 120 is covered by a first sleeve 127, whereas the second holder 130 is covered by a second sleeve 129. The first sleeve 127 fully envelops or encompasses the first holder 120 and the second sleeve 129 fully envelops or encompasses the second holder 130. The first and second sleeves 127, 129 are removed before deployment of the first and second fastening assemblies 510, 510', as discussed further below in detail.

Figure 3:
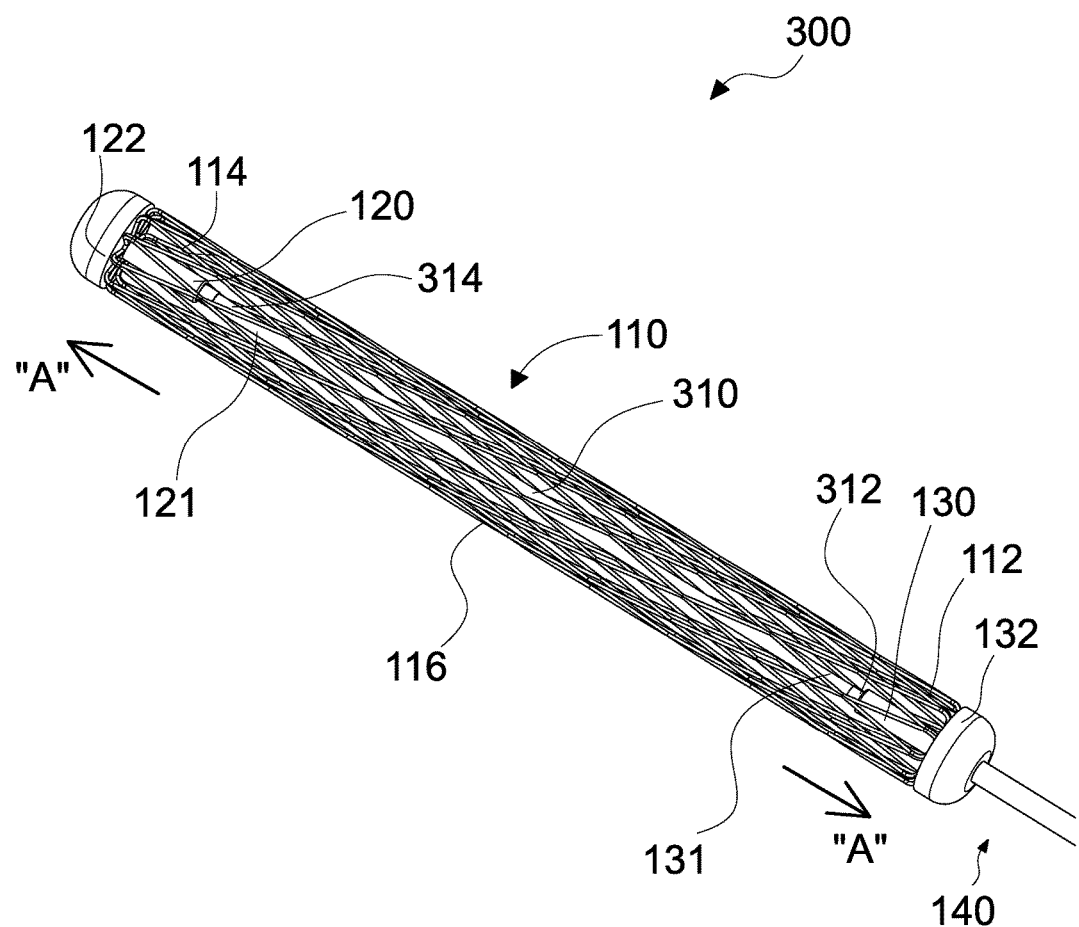
FIG. 3 illustrates the stent of FIG. 1 in an axially extended configuration before introduction into a lumen, in accordance with an embodiment of the present disclosure.

FIG. 3 illustrates the stent 110 of FIG. 1 in an extended configuration 300 before introduction into a lumen, in accordance with an embodiment of the present disclosure.

To deploy the stent 110, the stent 110 is axially extended, in a direction "A," as shown in FIG. 3. When the stent 110 is axially extended in the direction "A," the shaft 310 connecting the first holder 120 to the second holder 130 is also extended via one or more of the telescoping sections 141, 143, 145, 147, 149, 151 (FIG. 1). A first end 312 of the shaft 310 is connected to one end 131 of the second holder 130, whereas a second end 314 of the shaft 310 is connected to one end 121 of the first holder 120. This is further illustrated in FIG. 8 below. After the stent 110 has been extended, it is then introduced to lumen 400, as shown in FIG. 4. Thus, the deployment device 100 of FIG. 1 is configured to axially extend or stretch the stent 110 positioned thereon before the stent 110 is deployed to a desired location for securement within lumen 400 (FIG. 4).

FIG. 4 illustrates the stent 110 of FIG. 3 positioned within a deployment location of the lumen 400, in accordance with an embodiment of the present disclosure.

The stent 110, once axially extended, is then introduced into the lumen 400 into which it is to be deployed, navigated through the lumen 400 to a deployment location, typically a diseased artery, as shown in FIG. 4. The lumen 400 has a first region 410 and a second region 420. A portion of the stent 110 is placed within the first region 410 and another portion of the stent 110 is placed within the second region 420 such that the central point 125 or center region 116 of the stent 110 is placed at the center region 430 of the lumen 400. The center region 430 of the lumen 400 is the anastomosis region. As a result, the first holder 120 and the first protective cover 122 are positioned in the first region 410 of the lumen 400, and the second holder 130 and the second protective cover 132 are positioned in the second region 420 of the lumen 400. The shaft 310 is positioned in both the first and second regions 410, 420, such that the midpoint of the shaft 310 is placed in the center region 430. After placement of the stent 110 at the deployment location in the lumen 400, the stent 110 is deployed as shown in FIG. 5 described below.

FIG. 5 illustrates first and second protective covers 122, 132 of the stent 110 of FIG. 3 removed in order to commence deployment of the stent 110 within the lumen 400, in accordance with an embodiment of the present disclosure.

In FIG. 5, the first protective cover 122 and the second protective cover 132 are translated away from the stent deployment device 100 in a direction "B," via one or more of the telescoping sections 141, 143, 145, 147, 149, 151 (FIG. 1). After separation, the first protective cover 122 is still within the first region 410 of the lumen 400 and the second protective cover 132 is still within the second region 420 of the lumen 400. The center point 125 or central region 116 of the stent 110 is still positioned at the center region 430 of the lumen 400.

After separation of the first and second protective covers 122, 132, the first and second fastening assemblies 510, 510' are exposed. The first and second fastening assemblies 510, 510' extend from the first and second holders 120, 130, respectively. The first and second fastening assemblies 510, 510' are non-attachably engaged to an inner surface of the first and second protective covers 122, 132. The first and second fastening assemblies 510, 510' slide out of the first and second protective covers 122, 132. The first and second fastening assemblies 510, 510' may be a plurality of anchors, as described below with reference to FIGS. 6 and 7.

Figure 6:
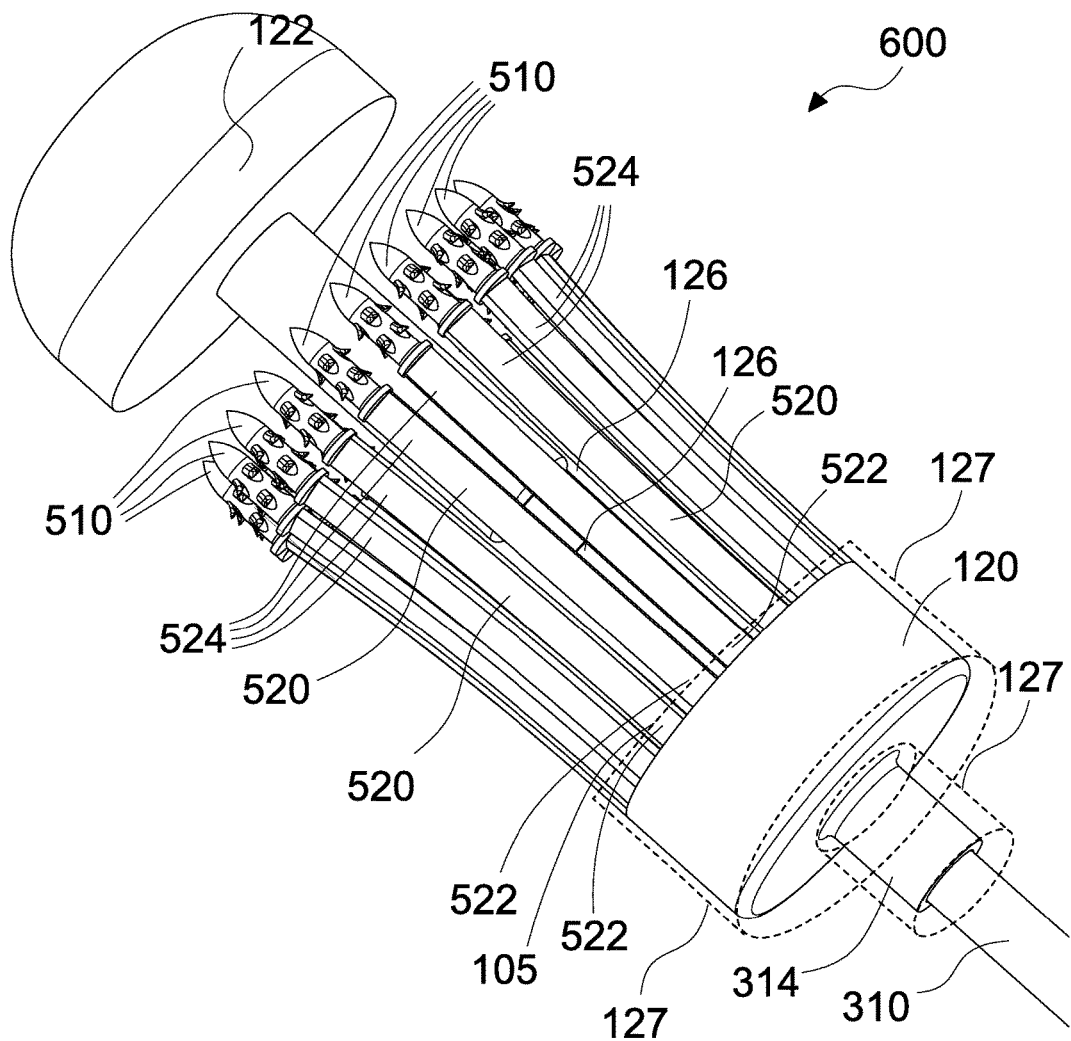
FIG. 6 illustrates a perspective view of one end of the stent holder depicting a plurality of anchors released therefrom, in accordance with an embodiment of the present disclosure.

FIG. 6 illustrates a perspective view 600 of one end of the first holder 120 depicting a plurality of anchors 510 released therefrom, in accordance with an embodiment of the present disclosure.

In FIG. 6, the first protective cover 122 has been extended to expose the first fastening assembly 510. The first fastening assembly 510 includes a plurality of anchors. Each anchor 510 is mounted on a distal end 524 of an extension 520. The extensions 520 may also be referred to as fingers. Each extension 520 has a proximal end 522 and a distal end 524. The extensions 520 are separated from each other by gaps 126. The gaps 126 extend the length of the extensions 520. The extensions 520 may be flexible in order to bend in a radial direction (FIG. 8).

The first holder 120 is a substantially cylindrical enclosure, where the plurality of anchors 510 are circumferentially positioned therein. The plurality of anchors 510 extend beyond the distal tip 105 of the first holder 120. Additionally, a distal portion 524 of each extension 520 extends beyond the distal tip 105 of the first holder 120. The extensions 520 are substantially parallel to each other in an initial configuration. One skilled in the art may contemplate any number of anchors suitable to hold one end of the stent 110 to an inner wall of the lumen 400.

Each anchor 510 has an opening 542 (FIG. 7) at its proximal end to attach it on the distal tip 524 of the extension 520. The anchor 510 may not be permanently attached to the extension 520. The plurality of anchors 510 are secured to the extensions 520 by the protective caps or first and second protective covers 122, 132 in an initial state to keep the extensions 520 parallel in an initial state. Subsequently, when deployment of the stent 110 is desired and the stent 110 has been placed within the lumen 400 (FIG. 5), the sleeve 127 is squeezed as described below, and the first holder is moved in a direction "B" (FIG. 5) in order to expose the plurality of anchors 510 secured on the distal ends 524 of the extensions 520. The plurality of anchors 510 are securely attached to their respective extensions 520 and are configured to radially expand to be secured to the lumen 400 (FIG. 5). The radial expansion of the plurality of anchors 510 will be described below with reference to FIG. 8.

FIG. 6 also depicts the sleeve 127 (shown in phantom) enveloping the first holder 120. The sleeve 127 extends from a proximal end to a distal end of the first holder 120. The sleeve 127 also covers the end 314 of the first holder 120 that is connected to shaft 310. The extensions 520 are kept together across the length of the first holder 120 and the sleeve 127. The sleeve 127 may be referred to as a squeezing sleeve. The sleeve 127 is removed from the first holder 120 by squeezing or applying a force on opposed ends of the sleeve 127. Once the sleeve 127 is removed from the first holder 120, the plurality of anchors 510 are actuated in an outward direction "R," as described below with reference to FIG. 8.

Moreover, the first and second holders 120, 130, the sleeve 127, and the first and second protective covers 122, 132 may be independently driven by a series of concentric and hollow tubes (not shown). For simplicity and sake of clarity, a single shaft 310 has been shown. However, it is also contemplated that the first and second protective covers 122, 132 are simultaneously driven by one or more concentric or hollow tubes or strings or cables. One skilled in the art may contemplate a variety of different driving mechanisms via one or more of the telescoping sections 141, 143, 145, 147, 149, 151 (FIG. 1).

Figure 7:
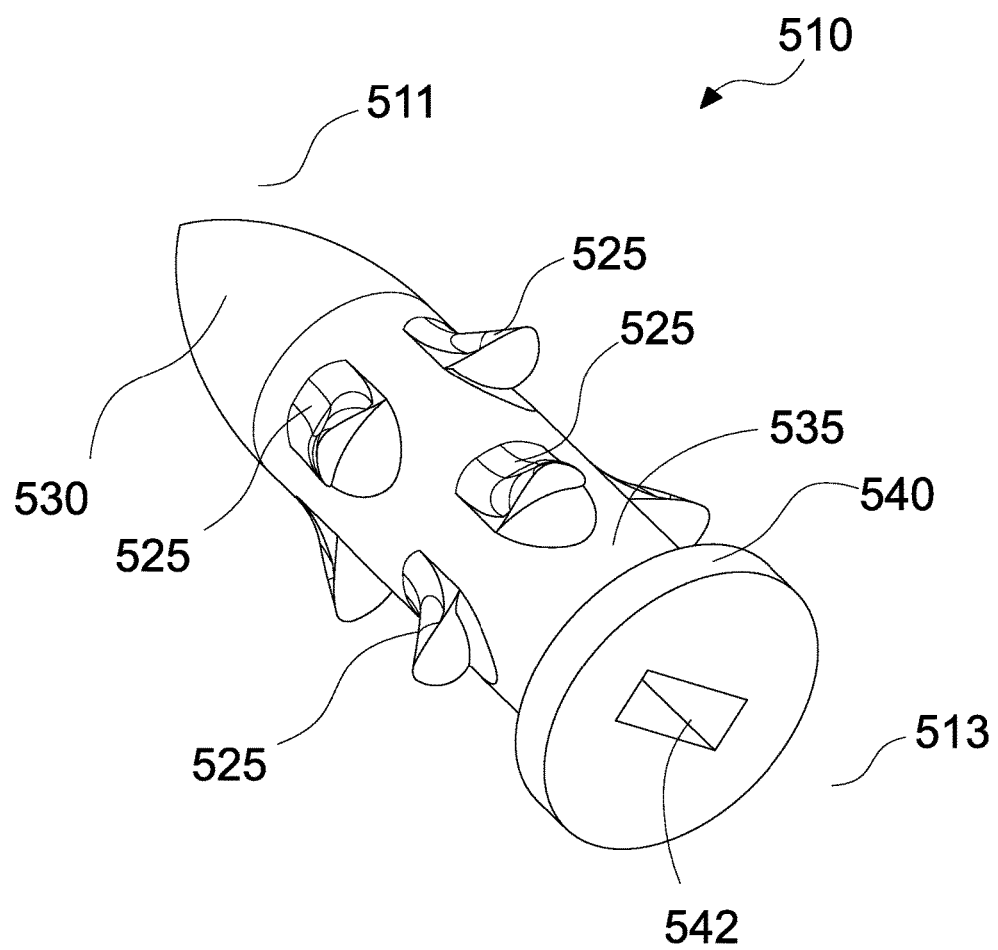
FIG. 7 illustrates an anchor of the stent holder for holding the stent of FIG. 1, in accordance with an embodiment of the present disclosure.

FIG. 7 illustrates an anchor 510 of the first holder 120 for holding the stent 110 of FIG. 1, in accordance with an embodiment of the present disclosure.

The anchors 510 of the first holder 120 are the same as the anchors 510' of the second holder 130. Thus, FIG. 7 could equally apply to the anchors 510' of the second holder 130. Referring to the first holder 120, the anchor 510 has a distal end 511 and a proximal end 513. The proximal end 513 includes an opening 542. A distal end of extension 520 (FIG. 6) is received within the opening 542 in order to secure the anchor 510 to the extension 520. The opening 542 is defined within a base 540. The base 540 is connected to a body portion 535, which in turn is connected to a tip portion 530. Each base 540 of each anchor 510 is configured to circumferentially engage one end of the stent 110, whereas each base 540 of each anchor 510' is configured to circumferentially engage the other end of the stent 110. Thus, the body portion 535 is configured to travel through the ends of the stent 110 such that each base 540 of each anchor 510, 510' latches on to the ends of stent 110. In this way, the base 540 of each anchor 510, 510' pushes the ends of the stent 110 toward the lumen 400 for attachment thereof. The attachment to the lumen 400 is a result of engagement between the lumen 400 and the barbs 525 of the body portion 535, as described below.

Figure 10:
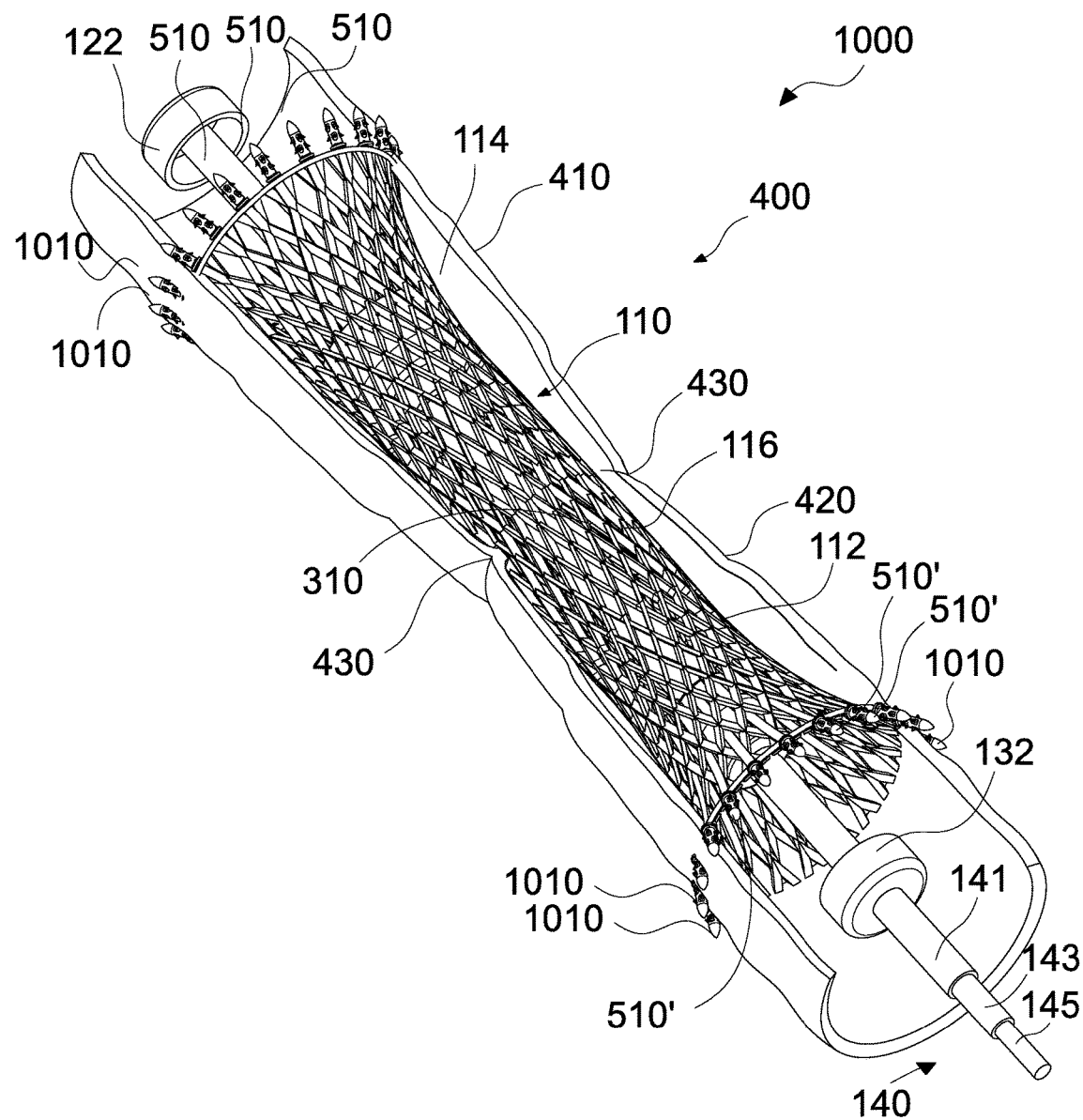
FIG. 10 illustrates the expanded stent with the anchors deployed to position the stent within the lumen, in accordance with an embodiment of the present disclosure.
Figure 11A:
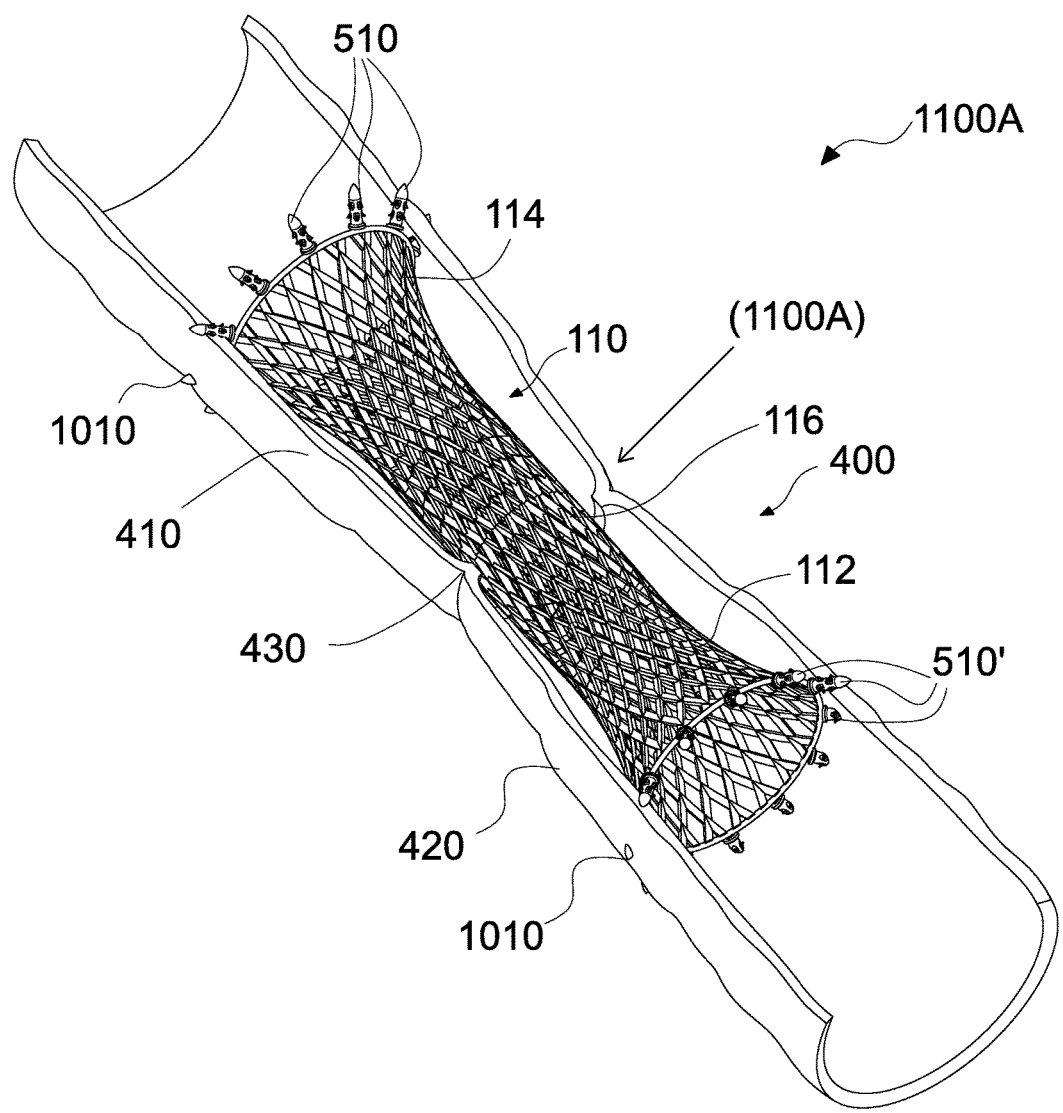
FIGS. 11A and 11B illustrate the stent anchored to the interior wall of the lumen via the plurality of anchors, in accordance with an embodiment of the present disclosure.
Figure 11B:
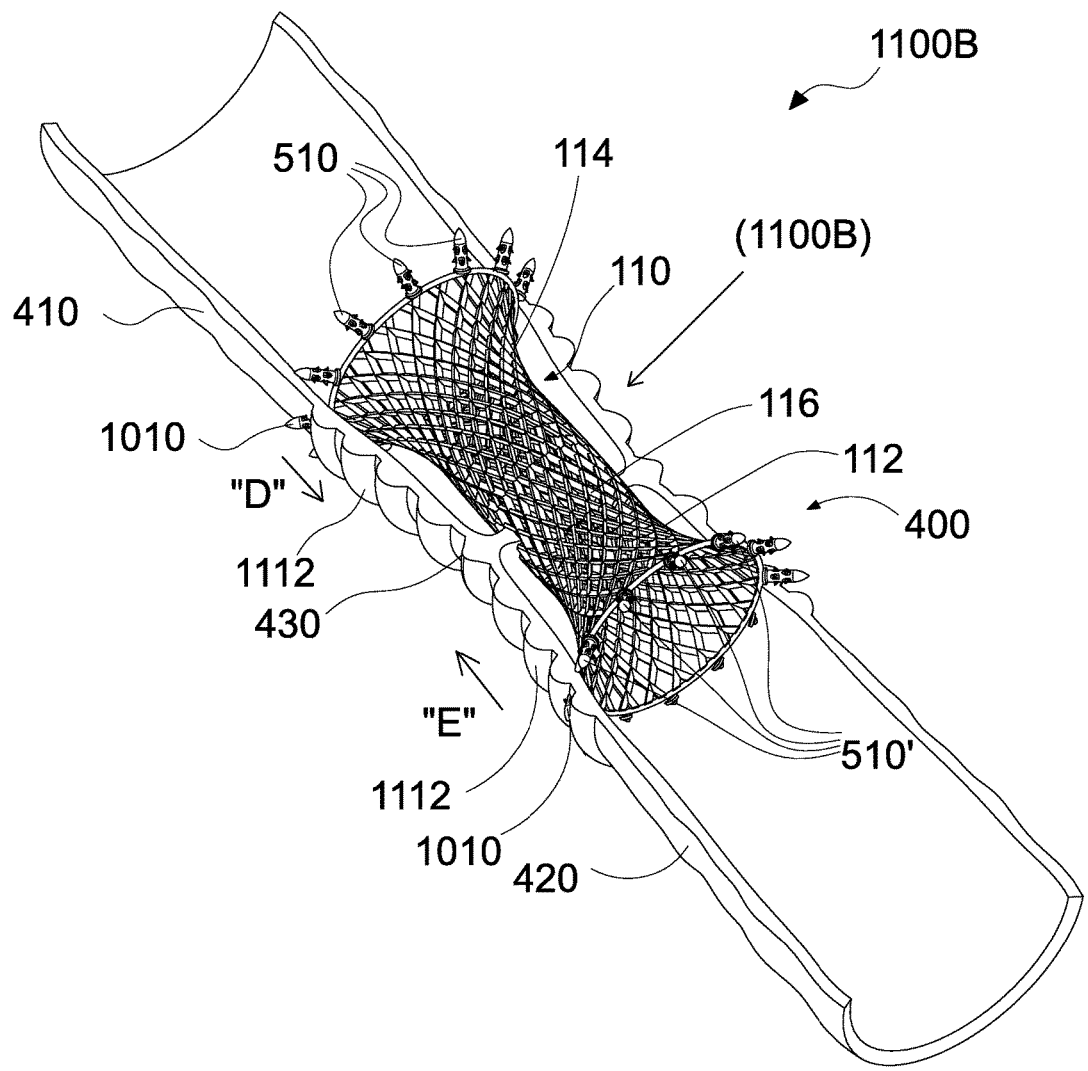

The body portion 535 may include a plurality of projections 525 or barbs. The plurality of projections 525 may be offset from each other across the length of the body portion 535. The tip portion 530 may have a smooth surface. The plurality of projections 525 aid in attaching the anchor 510 to the inner wall of the lumen 400 (FIG. 10). In use, the stent 110 is pressed into the inner wall of the lumen 400 so that the plurality of barbs 525 penetrate the lumen 400 and emerge from the other side where they are then locked in place (FIGS. 10, 11A, 11B). The plurality of barbs 525 prevent the stent 110 from dislodging from the lumen 400 at the deployment location. The barbs 525 may be degradable such that the stent 110 would slough off and be passed by a patient after the anastomosis is healed.

FIG. 8 illustrates radial deployment of the anchors 510, 510' of the first and second holders 120, 130 in accordance with an embodiment of the present disclosure.

When the first sleeve 127 and the second sleeve 129 are removed from the first and second holders 120, 130, respectively, via one or more of the telescoping sections 141, 143, 145, 147, 149, 151 (FIG. 1), the extensions 520 of each of the first and second holders 120, 130 are actuated or propelled to extend away from the first and second holders 120, 130 in a radial direction "R" to engage the lumen 400 (FIG. 10). The first and second holders move in a direction "C" along the longitudinal axis "X" in order to expose the extensions 520. Movement may be triggered by one or more of the telescoping sections 141, 143, 145, 147, 149, 151 (FIG. 1).

FIG. 8 clearly shows one end 121 of the first holder 120 connected to one end 131 of the second holder 130 via the shaft 310. The stent holding assembly 150 may expand in the axial direction "X" in order to expose the extensions 520 having the plurality of anchors 510, 510'. Moreover, a first end 312 of the shaft 310 is connected to one end 131 of the second holder 130, whereas a second end 314 of the shaft 310 is connected to one end 121 of the first holder 120.

The plurality of first anchors 510 are circumferentially positioned within the first holder 120 and the plurality of second anchors 510' are circumferentially positioned within the second holder 130. The plurality of first and second anchors 510, 510' are released from the first and second holders 120, 130 such that they maintain their circumferential nature. This results in a radial expansion "R," but no linear movement.

Figure 9:
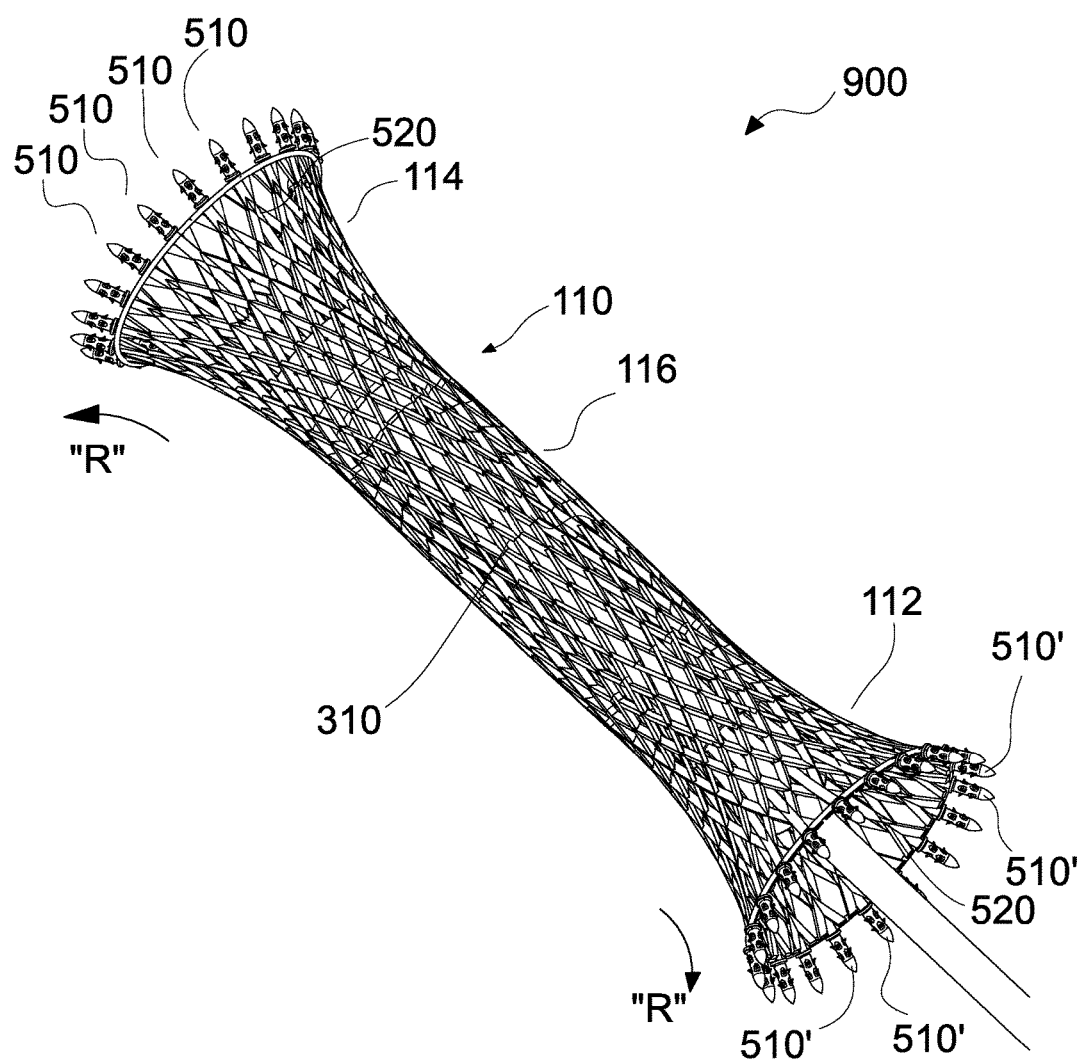
FIG. 9 illustrates radial expansion of the stent of FIG. 3 when the anchors of the stent holders are deployed, in accordance with an embodiment of the present disclosure.

FIG. 9 illustrates an expanded state 900 of the stent 110 of FIG. 3 when the anchors 510, 510' of the first and second holders 120, 130 are deployed, in accordance with an embodiment of the present disclosure.

The stent 110 expands in a radial direction "R". The plurality of first anchors 510 of the first holder 120 engage the distal end 114 of the stent 110, whereas the plurality of second anchors 510' of the second holder 130 engage the proximal end 112 of the stent 110. The plurality of first anchors 510 penetrate through the distal end 114 of the stent 110 and the plurality of second anchors 510' penetrate through the proximal end 112 of the stent 110. The plurality of projections 525 (FIG. 7) of each of the plurality of first and second anchors 510, 510' aid in holding the plurality of first and second anchors 510, 510' in place. The plurality of projections 525 enable the piercing of tissue and resulting securement to the lumen 400 (FIG. 10). The plurality of extensions 520 of each of the first and second holders 120, 130 are in a fully extended state.

Each base 540 of each anchor 510 is configured to circumferentially engage one end of the stent 110, whereas each base 540 of each anchor 510' is configured to circumferentially engage the other end of the stent 110. Thus, as noted, the body portion 535 is configured to travel through the ends of the stent 110 such that each base 540 of each anchor 510, 510' latches on to the ends of stent 110. In this way, the base 540 of each anchor 510, 510' pushes the ends of the stent 110 toward the lumen 400 for attachment thereof. The attachment to the lumen 400 is a result of engagement between the lumen 400 and the barbs 525 of the body portion 535, as illustrated in FIG. 10.

FIG. 10 illustrates the expanded stent 110 with the plurality of anchors 510, 510' deployed to an anchoring position 1000 where the expanded stent 110 is secured within the lumen 400, in accordance with an embodiment of the present disclosure.

In the anchoring position 1000, the central region 116 of the stent 110 is placed at the center region 430 of the lumen 400. The center region 430 of the lumen 400 is the anastomosis region. The plurality of first and second anchors 510, 510' extend through the lumen 400 at penetration regions 1010. The plurality of first and second anchors 510, 510' are secured to the lumen 400 at the penetration regions 1010 via the plurality of projections 525 (FIG. 7) that inhibit the plurality of first and second anchors 510, 510' from being withdrawn through tissue, as discussed above with reference to FIG. 9. The plurality of first and second anchors 510, 510' circumferentially penetrate the lumen 400 at penetration regions 1010. It is contemplated that the plurality of first and second anchors 510, 510' partially extend through those tissue regions.

FIGS. 11A and 11B illustrate the stent 110 anchored to the interior wall of the lumen 400 via the plurality of first and second anchors 510, 510', in accordance with an embodiment of the present disclosure.

In FIG. 11A, in a first configuration 1100A, the anastomosis is under tension, while the stent 110 is in the extended state 1110A and anchored to the first region 410 of the lumen 400, the first region 410 circumferentially extending around the lumen 400. In FIG. 11B, in a second configuration 1100B, the anastomosis is in a first state, while the stent 110 is also in the first state 1110B. When the anastomosis is in the first state, the stent 110 pulls the first region 410 of the lumen 400 in a direction "D" and pulls the second region 420 of the lumen 400 in a direction "E." When the first and second regions 410, 420 of the lumen 400 are drawn toward each other (i.e., towards center region 430), an accordion-like configuration 1112 is formed around the center region 430 of the lumen 400. The accordion-like configuration 1112 is present on both sides of the center region 430. As a result, the stent deployment device 100 provides a means of axially stretching the stent 110 and attaching it to the wall of the lumen 400 in a stretched or axially expanded state. Thus, once the stent deployment device 100 is removed from the lumen 400, the stent 110 contracts axially, thus reducing tension on the staple or suture line. This further promotes healing and minimizes the risk of leaks.

In summary, FIGS. 1-11B provide for a stent 110 and stent deployment device 100 that minimizes tension, thus contributing to proper healing of tissue without any leaks by reducing tensile forces applied to the anastomotic site. The stent 110 may be made from absorbable or non-absorbable material, and expands in an axial direction, as well as in a radial direction. Also, the stent 110 may be made from a deformable metal or plastic scaffolding, which is covered by an impermeable lining material. The metal or plastic may be degradable or non-degradable. The impermeable lining may be made from an elastomeric polymer. The stent deployment device 100 thus stretches, inserts, and anchors the stent 110 to the inner walls of a lumen 400 with a plurality of fasteners or anchors 510, 510'.

Moreover, the axial elongation of the stent 110 causes radial compression when the stent 110 is being inserted into the lumen 400. Once the stent 110 is anchored, removing the stent delivery system 100 allows the stent 110 to axially compress and radially dilate, which maintains patency and a tension free joint. This is achieved, for example, by the shape of the stent body's mesh and memory.

In an initial configuration, the stent 110 is in a first state on the stent deployment device 100 (FIG. 1). The stent 110 is secured to first and second protective covers 122, 132 and the stent 110 may be independently driven by the first and second holders 120, 130. The stent 110 is axially expanded or stretched before being inserted into the lumen 400 (FIG. 3). The stent 110 is positioned within the lumen 400 with its center region 116 at the anastomosis region (FIG. 4). The first and second protective covers 122, 132 protect the organs when the stent deployment device 100 is inserted and manipulated in the lumen 400. After the first and second protective covers 122, 132 are separated from the stent 110 (FIG. 5), via one or more of the telescoping sections 141, 143, 145, 147, 149, 151 (FIG. 1), the stent deployment device 100 expands the stent 110 in a radial direction "R," and the stent 110 is attached or secured to the lumen 400 via the plurality of anchors 510, 510' (FIGS. 9-11B).

Each of the first and second stent holders 120, 130 includes a first and second sleeve 127, 129, respectively (FIG. 2). The extensions 520 having the plurality of anchors 510, 510' at distal ends 524 thereof are circumferentially positioned with the first and second holders 120, 130 (FIG. 8). The extensions 520 are kept together by the full depth of the sleeves 127, 129. Each of the plurality of first and second anchors 510, 510' includes an opening 542 for placement on the distal ends 524 of the extensions 520 (FIG. 7). The plurality of first and second anchors 510, 510' are secured to the extensions 520 by the first and second protective covers 122, 132 in the initial state (FIG. 4). The sleeves 127, 129 and the first and second protective covers 122, 132 may be independently driven by a series of concentric or hollow tubes. A central tube or shaft 310 may house a scope, a guide wire, or any other additional instruments (not shown). The plurality of first and second anchors 510, 510' are then radially deployed when the sleeves 127, 129 are removed from the first and second holders 120, 130, respectively, via one or more of the telescoping sections 141, 143, 145, 147, 149, 151 (FIG. 1), thus exposing the extensions 520, while the extensions 520 are under tension resulting from the expanded stent 110 (FIG. 8). The anchoring of the stent 110 to the lumen 400 is fully controlled by the amount of exposition of the extensions 520 and by the sequence of deployment (FIGS. 10-11B). Simultaneous or individual deployment may be available. Once the stent 110 is anchored and in place, the extensions 520 retract and disengage the plurality of first and second anchors 510, 510' via one or more of the telescoping sections 141, 143, 145, 147, 149, 151 (FIG. 1). Now the clinician can remove the stent deployment device 100 and leave the stent 110 in place.

FIGS. 12A-16B described below present alternative embodiments of stent and stent deployment devices.

Figure 12A:
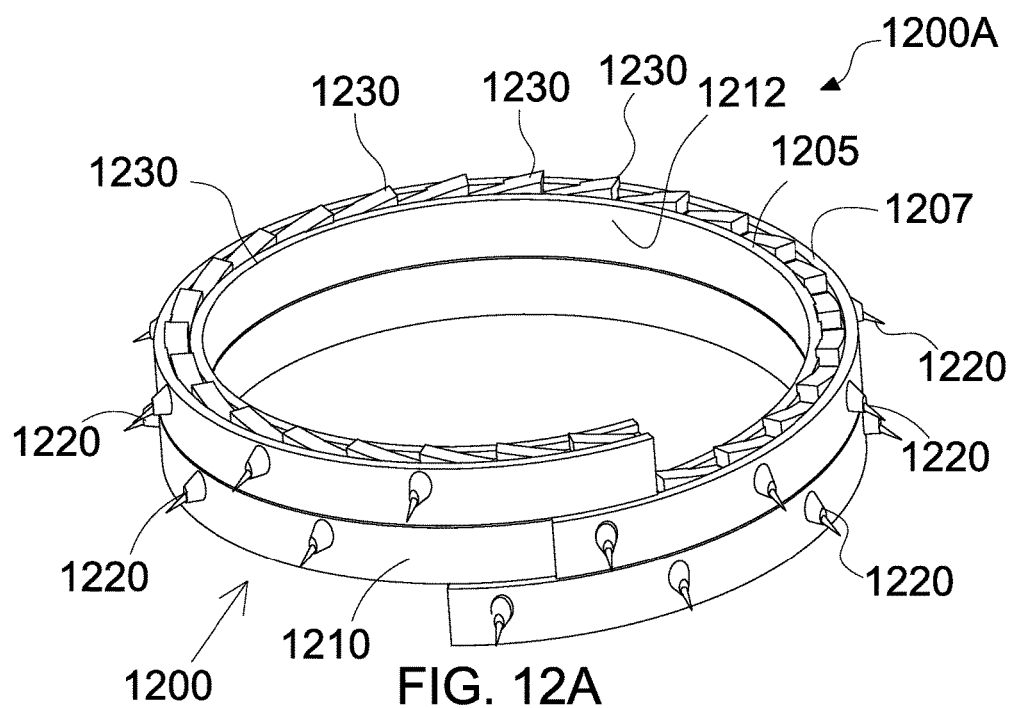
FIGS. 12A and 12B illustrate another embodiment of an anchor for securing a stent to a lumen, in accordance with an embodiment of the present disclosure.
Figure 12B:
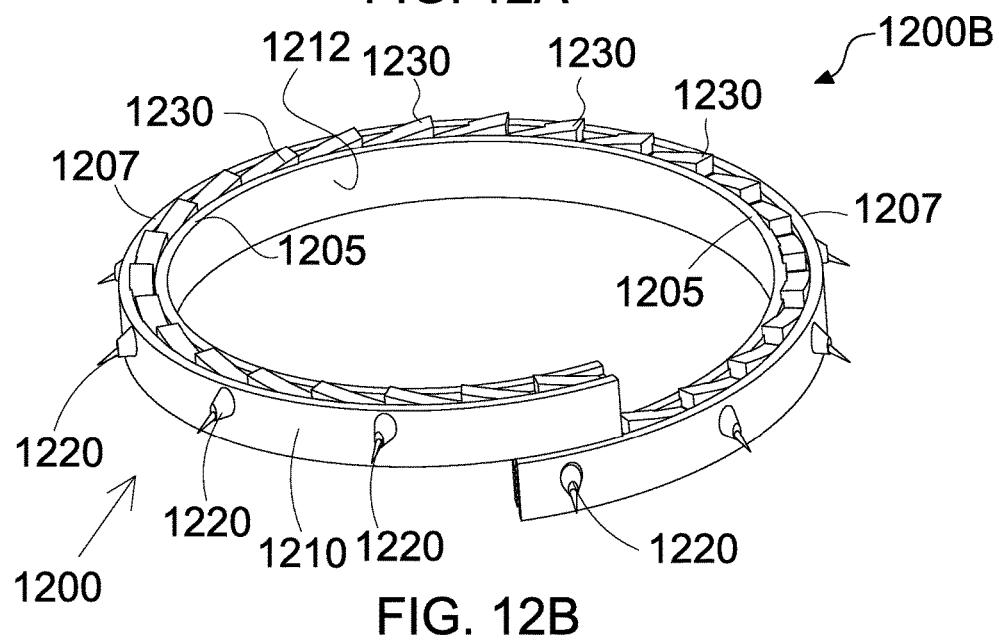

FIGS. 12A and 12B illustrate another embodiment for securing a stent 110 to a lumen 400 via an anchor ring 1200 (FIGS. 14A, 14B), in accordance with an embodiment of the present disclosure.

In a first configuration 1200A, the anchor ring 1200 is in a coiled state. The anchor ring 1200 is substantially circular with a plurality of spiked projections 1220 extending away from an outer surface 1210 of the anchor ring 1200. The anchor ring 1200 is formed by a first or inner ring section 1205 and a second or outer ring section 1207. The first ring section 1205 defines an inner surface 1212 of the anchor ring 1200 and the second ring section 1207 defines the outer surface 1210 of the anchor ring 1200. The first and second ring sections 1205, 1207 are separated from each other by a series of wedge-like members or teeth 1230. In a second configuration 1200B, the anchor ring 1200 is in a fully open or expanded state.

Figure 13A:
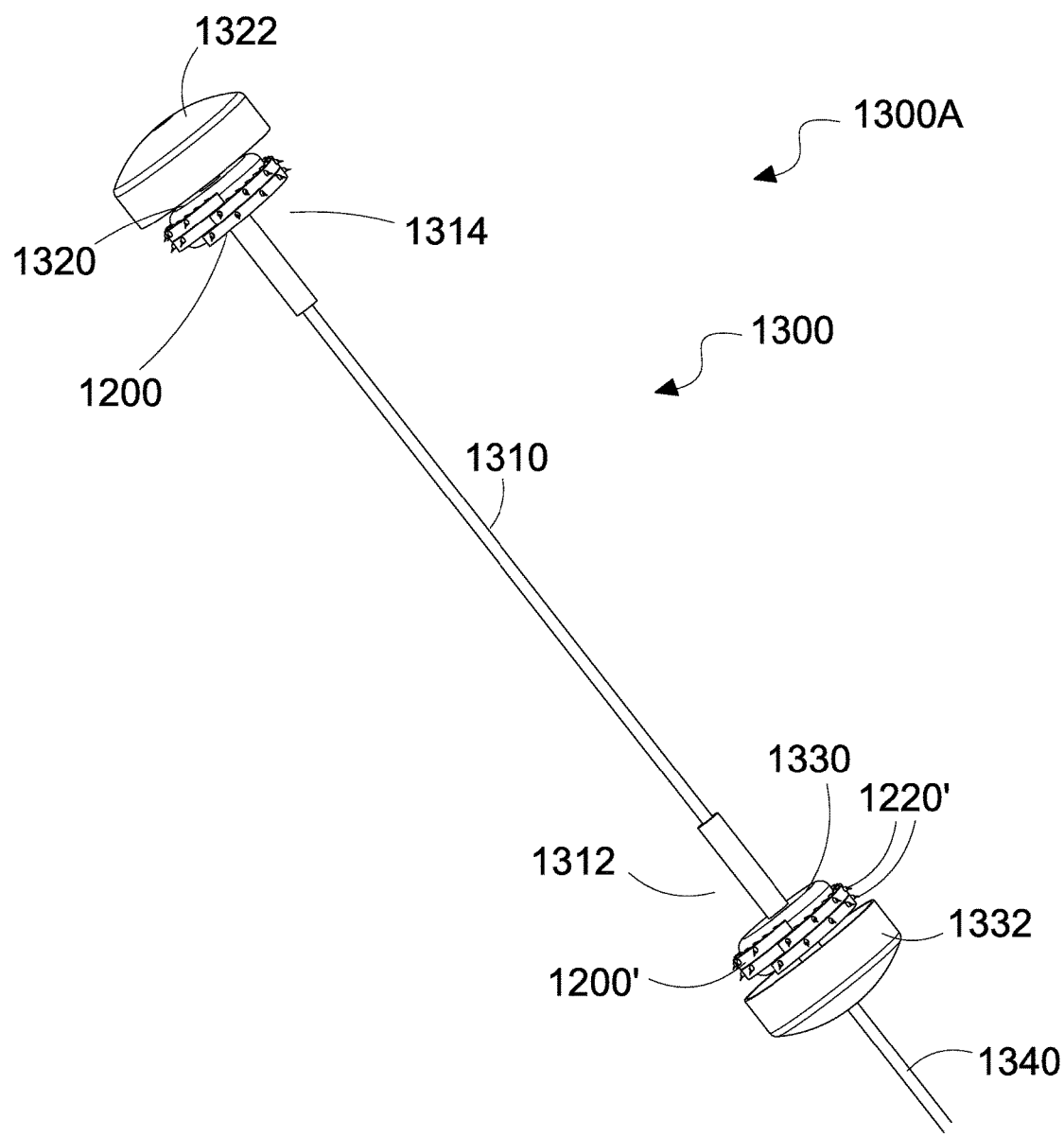
FIG. 13A illustrates the anchor of FIG. 12A mounted onto a stent deployment device including a pair of balloons when the balloons are in a collapsed/unexpanded configuration, in accordance with an embodiment of the present disclosure.
Figure 13B:
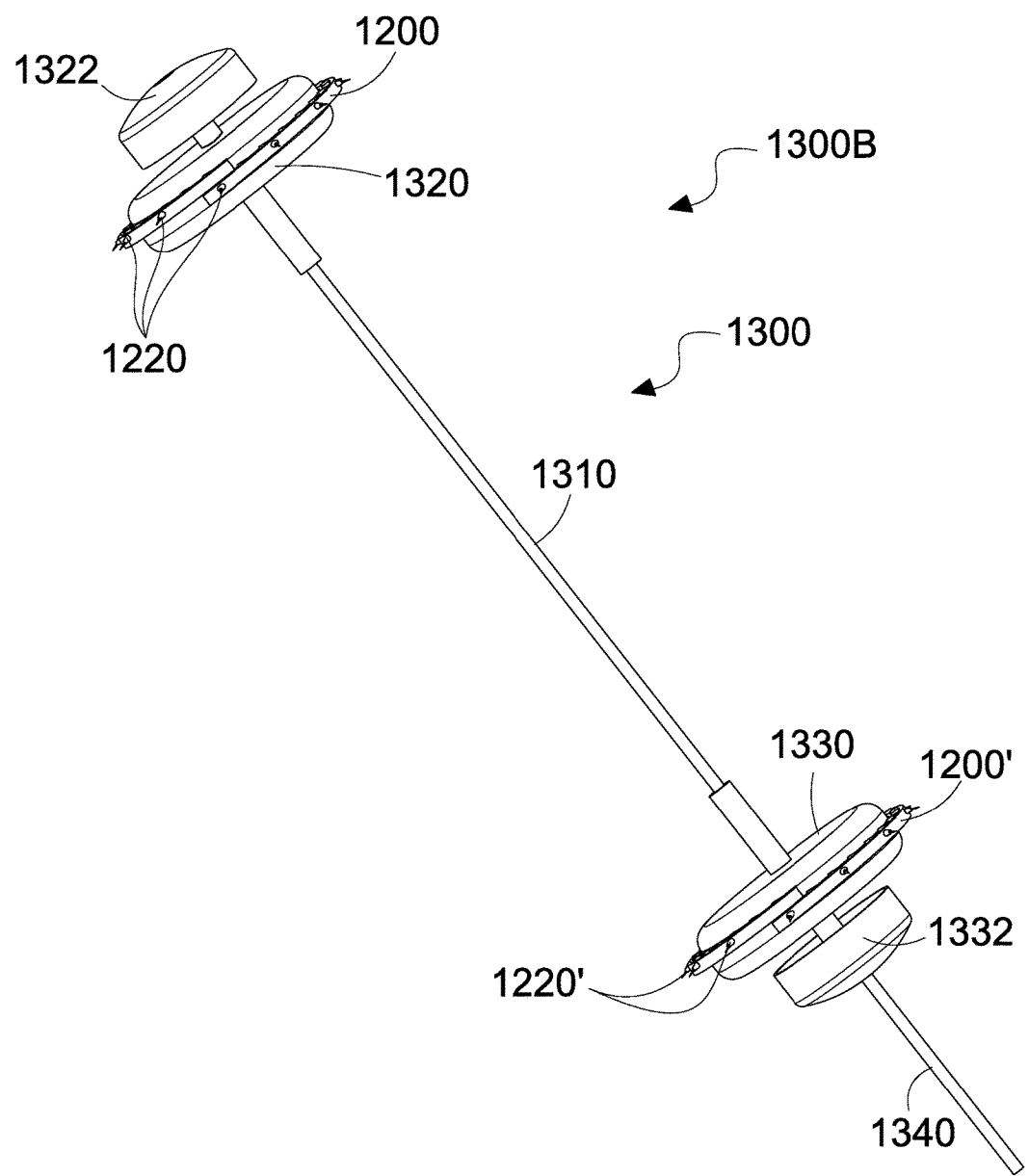
FIG. 13B illustrates the anchor of FIG. 12B mounted onto a stent deployment device including a pair of balloons when the balloons are in an expanded configuration, in accordance with an embodiment of the present disclosure.

FIGS. 13A and 13B illustrate the anchor ring 1200 of FIG. 12A mounted onto a stent deployment device 1300 including a pair of balloons 1320, 1330, both in an expanded and unexpanded configuration, in accordance with an embodiment of the present disclosure.

In FIG. 13A, the anchor rings 1200, 1200' are in a coiled configuration 1300A, whereas in FIG. 13B, the anchor rings 1200, 1200' are in a fully expanded configuration 1300B.

The stent deployment device 1300 includes a first protective cover 1322 connected to a second protective cover 1332 via a shaft 1310. At a distal end 1314 of shaft 1310 is mounted a first balloon 1320. At a proximal end 1312 of shaft 1310 is mounted a second balloon 1330. An anchor ring 1200 is wrapped around the first balloon 1320 and an anchor ring 1200' is wrapped around the second balloon 1330. The stent deployment device 1300 is attached to a handle body 1340.

In the first configuration 1300A of FIG. 13A, the balloons 1320, 1330 are in a deflated configuration, whereas in the second configuration 1300B of FIG. 13B, the balloons 1320, 1330 are in an expanded configuration. In the first configuration 1300A, the anchor rings 1200, 1200' are in a coiled configuration around the first and second balloons 1320, 1330, respectively. In the second configuration 1300B, the anchor rings 1200, 1200' are in an expanded configuration around the first and second balloons 1320, 1330, respectively. The spikes or projections 1220 of the first anchor ring 1200 and the spikes or projections 1220' of the second anchor ring 1200' extend away from the balloons 1320, 1330, respectively. The first and second balloons 1320, 1330 are inflated to expand the anchor rings 1200, 1200' disposed respectively thereon.

Figure 14A:
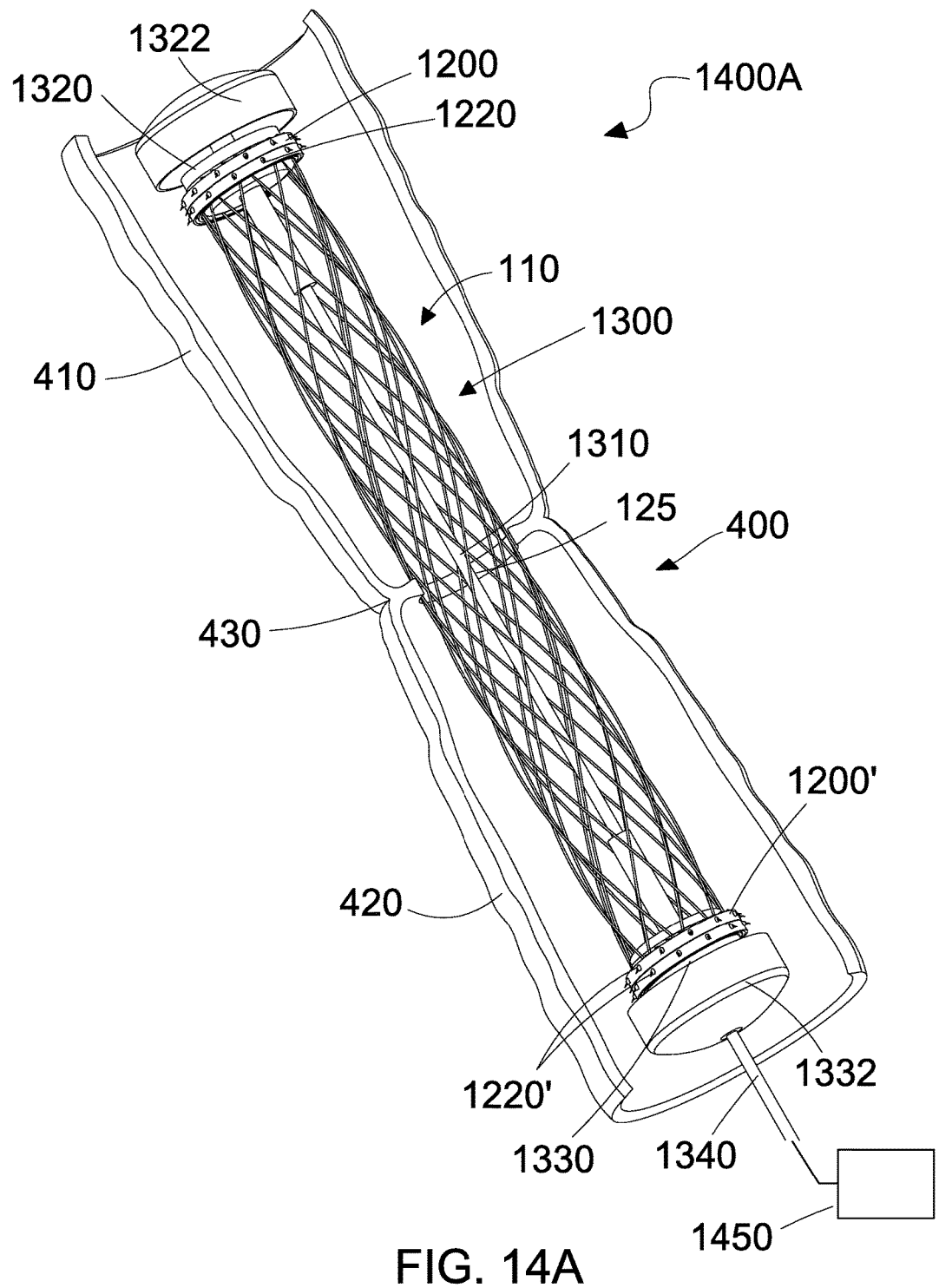
FIGS. 14A and 14B illustrate a stent deployment device employing the anchor of FIG. 12A, where the stent transitions from an unexpanded configuration to an expanded configuration, in accordance with an embodiment of the present disclosure.
Figure 14B:
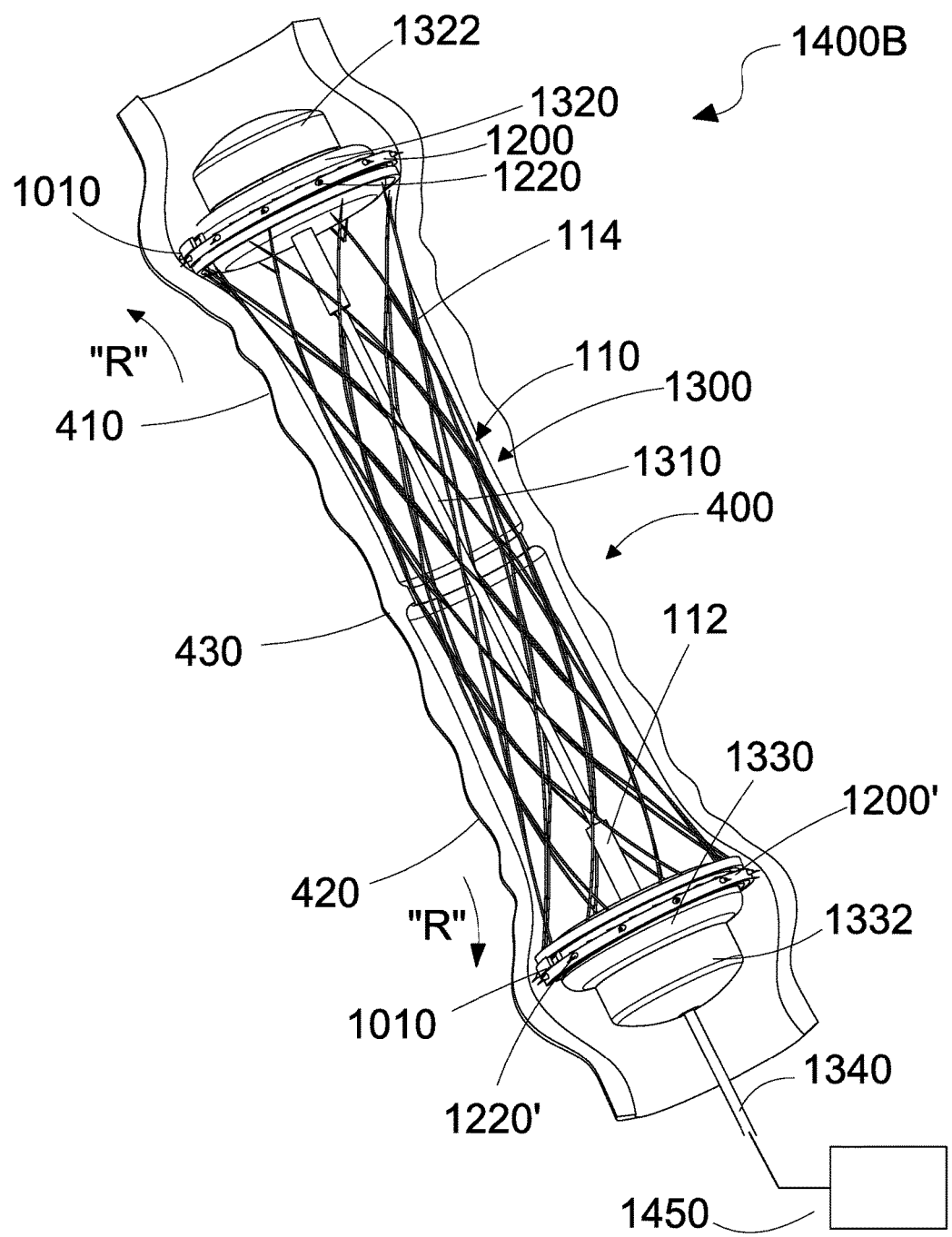

FIGS. 14A and 14B illustrate the stent deployment device 1300 of FIGS. 13A and 13B employing the anchor ring 1200 of FIGS. 12A and 12B, where the stent 110 transitions from an unexpanded configuration to an expanded configuration, in accordance with an embodiment of the present disclosure.

FIG. 14A depicts the stent deployment device 1300 positioned within a lumen 400 in an undeployed configuration 1400A, whereas FIG. 14B depicts the stent deployment device 1300 positioned within the lumen 400 in a deployed configuration 1400B.

The lumen 400 has a first region 410 and a second region 420. In the undeployed configuration 1400A, a portion of the stent 110 is placed within the first region 410 and another portion of the stent 110 is placed within the second region 420 such that the central point 125 of the stent 110 is placed at the center region 430 of the lumen 400. The center region 430 of the lumen 400 is the anastomosis region.

Thus, the first balloon 1320 with an anchor ring 1200 attached thereon is positioned in the first region 410 of the lumen 400, and the second balloon 1330 with an anchor ring 1200' attached thereon is positioned in the second region 420 of the lumen 400. The shaft 1310 is positioned in both the first and second regions 410, 420, such that the midpoint of the shaft 1310 is placed at the center region 430. After placement of the stent 110 at the deployment location in the lumen 400, the stent 110 is deployed as shown in FIG. 14B. A fluid source 1450 may be used to provide fluid to expand the balloons 1320, 1330, as described below with reference to FIG. 14B. The stent deployment device 1300 is attached to a handle body 1340.

In FIG. 14B, the first and second balloons 1320, 1330 expand via, for example, pressurized fluid supplied by a fluid source 1450. When the first balloon 1320 expands, the anchor ring 1200 attached thereto also uncoils. Similarly, when the second balloon 1330 expands, the anchor ring 1200' attached thereon also expands. The first balloon 1320 pushes the anchor ring 1200 against the inner wall of lumen 400 such that the plurality of spiked projections 1220 penetrate the lumen 400 to secure the anchor ring 1200 thereto. A portion of the first region 410 of the lumen 400 is also pushed such that its diameter at the penetration region 1010 is larger than the diameter on the lumen 400 in its first state.

Similarly, the second balloon 1330 pushes the anchor ring 1200' against the inner wall of lumen 400 at the penetration region 1010 such that the plurality of spiked projections 1220' penetrate the lumen 400 to secure the anchor ring 1200' thereto. A portion of the second region 420 of the lumen 400 is also pushed such that its diameter at the penetration region 1010 is larger than the diameter of the lumen 400 in its first state. Thus, the stent 110 expands in a radial direction "R" such that the stent 110 contacts or engages the inner wall of the lumen 400, as shown in FIG. 14B.

As a result, the stent deployment device 1300 provides a means of axially stretching the stent 110 and attaching it to the wall of the lumen 400 in a stretched or axially expanded state. Thus, once the stent deployment device 1300 is removed from the lumen 400, the stent 110 contracts axially, thus reducing tension on the staple or suture line. This further promotes healing and minimizes the risk of leaks. Therefore, tension can be reduced at the anastomosis site.

Figures 15A, 15B:
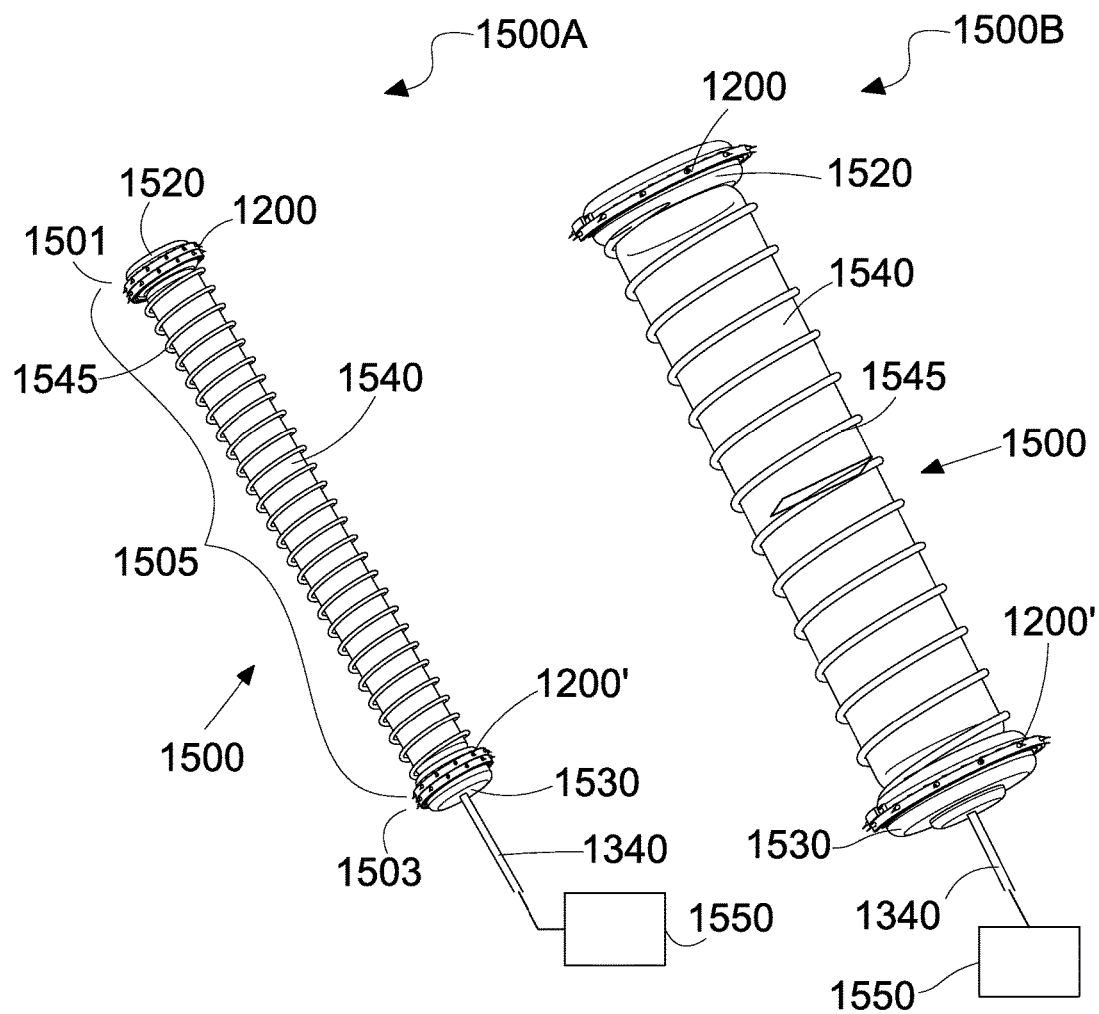
FIGS. 15A and 15B illustrate a stent deployment device having three balloons in a collapsed configuration and in an expanded configuration, respectively, in accordance with another embodiment of the present disclosure.

FIGS. 15A and 15B illustrate a stent deployment device 1500 having three balloons 1520, 1530, 1540, in accordance with another embodiment of the present disclosure.

The stent deployment device 1500 includes a handle body 1340 connected to stent holding assembly 1505. The stent holding assembly 1505 includes a first balloon 1520 at a distal end 1501 and a second balloon 1530 at a proximal end 1503. An anchor ring 1200 is positioned around the first balloon 1520 and an anchor ring 1200' is positioned around the second balloon 1530. The third balloon 1540 extends between the first and second balloons 1520, 1530. A coil spring 1545 extends circumferentially around the third balloon 1540 from a proximal end to a distal end thereof. The first, second, and third balloons 1520, 1530, 1540 may be inflated via, for example, pressurized fluid provided by a fluid source 1550. The first, second, and third balloons 1520, 1530, 1540 may be simultaneously or independently inflated via a plurality of fluid sources. For example, each balloon 1520, 1530, 1540 may be connected to its own fluid source.

FIG. 15A illustrates the balloons 1520, 1530, 1540 in a deflated state 1500A, whereas FIG. 15B illustrates the balloons 1520, 1530, 1540 in an expanded state 1500B. In the expanded state, the anchor ring 1200 of the first balloon 1520 expands and the anchor ring 1200' of the second balloon 1530 expands. Additionally, the third balloon 1540 expands such that the coil 1545 attached therearound expands.

Figures 16A, 16B:
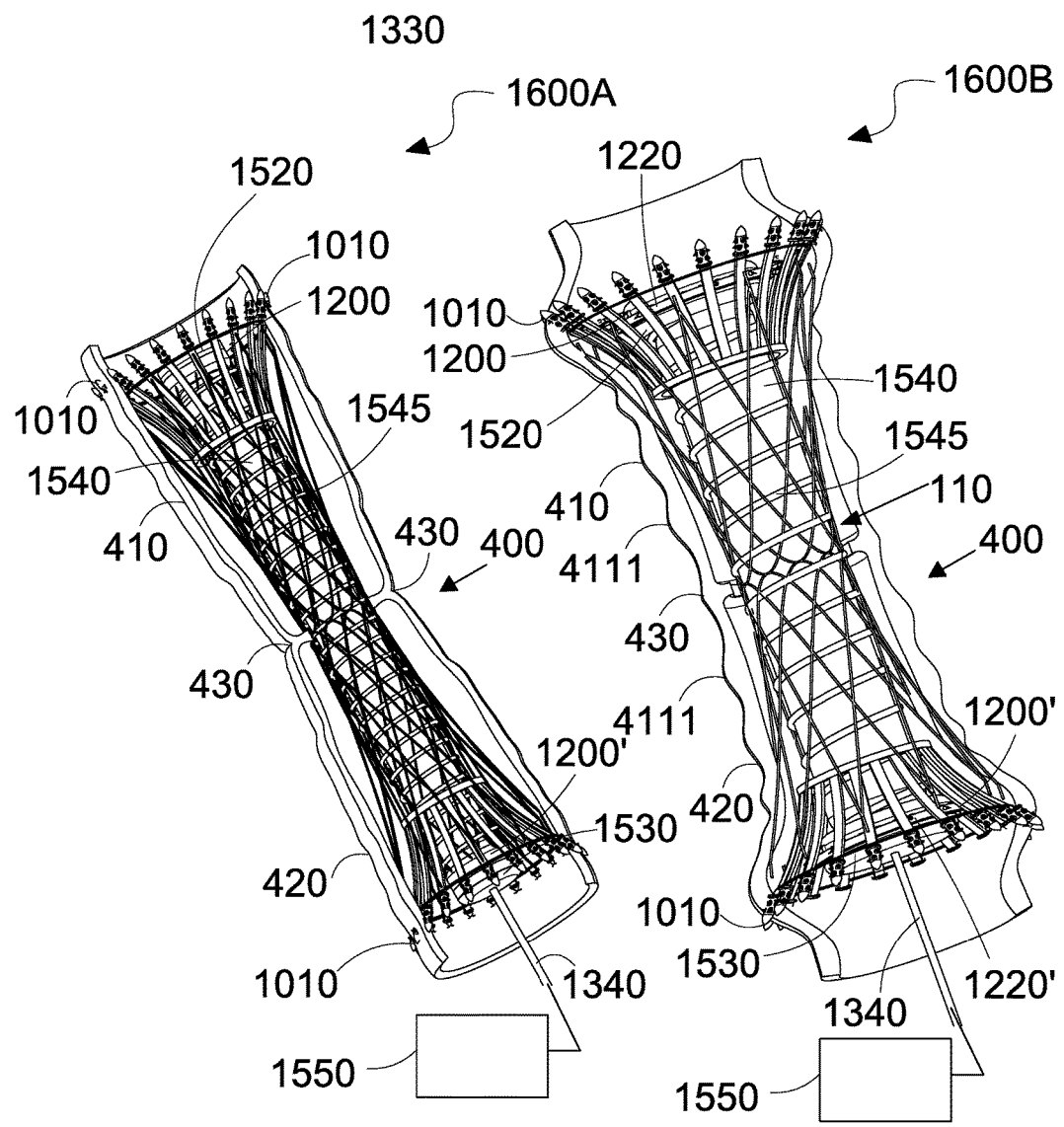
FIGS. 16A and 16B illustrate the stent deployment device of FIG. 15A, where the stent transitions from an unexpanded configuration to an expanded configuration within a lumen, in accordance with another embodiment of the present disclosure.

FIGS. 16A and 16B illustrate the stent deployment device 1500 of FIGS. 15A and 15B, where the stent 110 transitions from an unexpanded configuration to an expanded configuration within a lumen 400, in accordance with another embodiment of the present disclosure.

FIG. 16A depicts the stent deployment device 1500 positioned within a lumen 400 in an undeployed configuration 1600A, whereas FIG. 16B depicts the stent deployment device 1500 positioned within a lumen 400 in a deployed configuration 1600B.

The lumen 400 has a first region 410 and a second region 420. In the undeployed configuration 1600A, a portion of the stent 110 is placed within the first region 410 and another portion of the stent 110 is placed within the second region 420 such that the central point of the stent 110 is placed at the center region 430 of the lumen 400. The center region 430 of the lumen 400 is the anastomosis region.

Thus, the first balloon 1520 with an anchor ring 1200 attached thereon is positioned in the first region 410 of the lumen 400, and the second balloon 1530 with an anchor ring 1200' attached thereon is positioned in the second region 420 of the lumen 400. The third balloon 1540 is positioned in both the first and second regions 410, 420, such that the midpoint of the third balloon 1540 is placed at the center region 430. After placement of the stent 110 at the deployment location in the lumen 400, the stent 110 is deployed as shown in FIG. 16B and described below.

In FIG. 16B, the first, second, and third balloons 1520, 1530, 1540 expand via, for example, a pressurized fluid supplied by a fluid source 1550. When the first balloon 1520 expands, the anchor ring 1200 attached thereto also expands. Similarly, when the second balloon 1530 expands, the anchor ring 1200' attached thereon also expands. The third balloon 1540 also expands against the inner wall of the lumen 400. Expansion of the third balloon 1540 results in expansion of the coil 1545.

The first balloon 1520 pushes the anchor ring 1200 against the inner wall of lumen 400 such that the plurality of spiked projections 1220 penetrate the lumen 400 to secure the anchor ring 1200 thereto. A portion of the first region 410 of the lumen 400 is also pushed such that its diameter at the penetration region 1010 is larger than the diameter on the lumen 400 at its first state. Similarly, the second balloon 1530 pushes the anchor ring 1200' against the inner wall of lumen 400 at the penetration region 1010 such that the plurality of spiked projections 1220' penetrate the lumen 400 to secure the anchor ring 1200' thereto. A portion of the second region 420 of the lumen 400 is also pushed such that its diameter at the penetration region 1010 is larger than the diameter of the lumen 400 at its first state. Thus, the stent 110 expands in a radial direction such that the stent 110 contacts or engages the inner wall of the lumen 400, as shown in FIG. 16B. Additionally, the third balloon 1540 pushes against the inner wall of the lumen 400 across the length of the lumen 400.

When the first and second regions 410, 420 of the lumen 400 are drawn together, an accordion-like configuration 4111 (ripple effect) is formed around the center region 430 of the lumen 400. This ripple effect 4111 is not as pronounced as in FIG. 11B because of the third balloon 1540 which expands the central region of lumen 400. Thus, the pressure applied by the third balloon 1540 via the coil 1545 against the inner wall of the lumen 400 results in less stress applied to the lumen 400. As a result, the stent deployment device 1500 provides a means of axially stretching the stent 110 and attaching it to the wall of the lumen 400 in a stretched or axially expanded state. Thus, once the stent deployment device 1500 is removed from the lumen 400, the stent 110 contracts axially, thus reducing tension applied to the staple line or suture line (e.g., ripple effect 4111). This further promotes healing and minimizes the risk of leaks. Therefore, the tension can be reduced at the anastomosis site.

FIGS. 17-25 described below illustrate another embodiment of a stent and stent deployment devices.

Figures 17, 18:
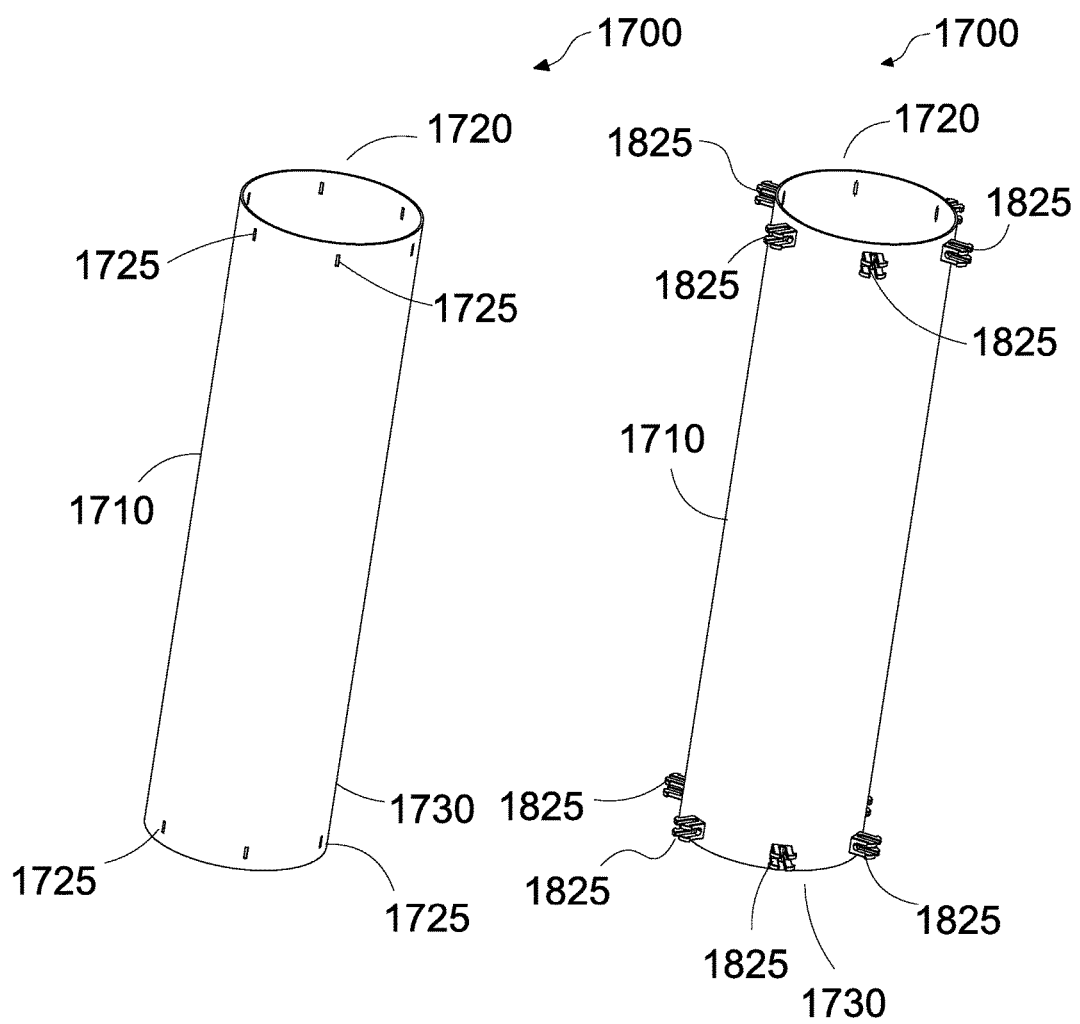
FIG. 17 illustrates a stent, in accordance with another embodiment of the present disclosure.
FIG. 18 illustrates the stent of FIG. 17 including a plurality of tacks attached at proximal and distal ends thereof, in accordance with an embodiment of the present disclosure.

FIG. 17 illustrates a stent 1700, in accordance with another embodiment of the present disclosure.

The stent 1700 has a body portion 1710 with a proximal end 1720 and a distal end 1730. The proximal end 1720 of the body portion 1710 has a plurality of openings 1725 and the distal end 1730 of the body portion 1710 has a plurality of openings 1725. The plurality of openings 1725 circumferentially extend around the proximal and distal ends 1720, 1730 of the body portion 1710. The stent 1700 may be an elastic stent.

FIG. 18 illustrates the stent 1700 of FIG. 17 including a plurality of tacks 1825 at proximal and distal ends 1720, 1730 thereof, in accordance with an embodiment of the present disclosure.

The plurality of tacks 1825 are inserted into openings 1725 of the stent 1700. The plurality of tacks 1825 extend away from the outer surface of the body portion 1710. The plurality of tacks 1825 may be equally spaced apart from each other. The plurality of tacks 1825 may be permanently or temporarily attached to the plurality of openings 1725 of the stent 1700.

Figure 19:
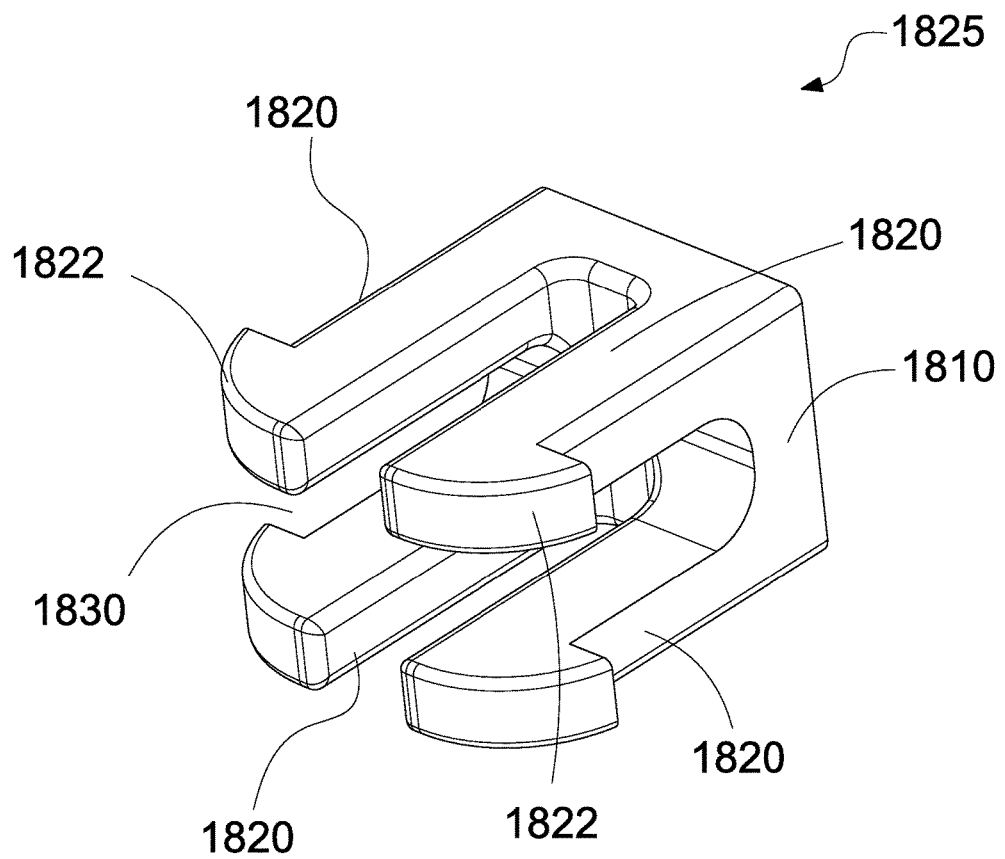
FIG. 19 illustrates a tack usable with the stent of FIG. 17, in accordance with an embodiment of the present disclosure.

FIG. 19 illustrates a tack 1825 for attachment to the proximal and distal ends 1720, 1730 of the stent 1700 of FIG. 17, in accordance with an embodiment of the present disclosure.

The tack 1825 has a body portion 1810 with four legs 1820 extending therefrom. The four legs 1820 extend from the corners of the tack 1825. The tip of each of the legs 1820 includes an arm 1822. The tack 1825 also includes a hollow interior region 1830.

Figure 20:
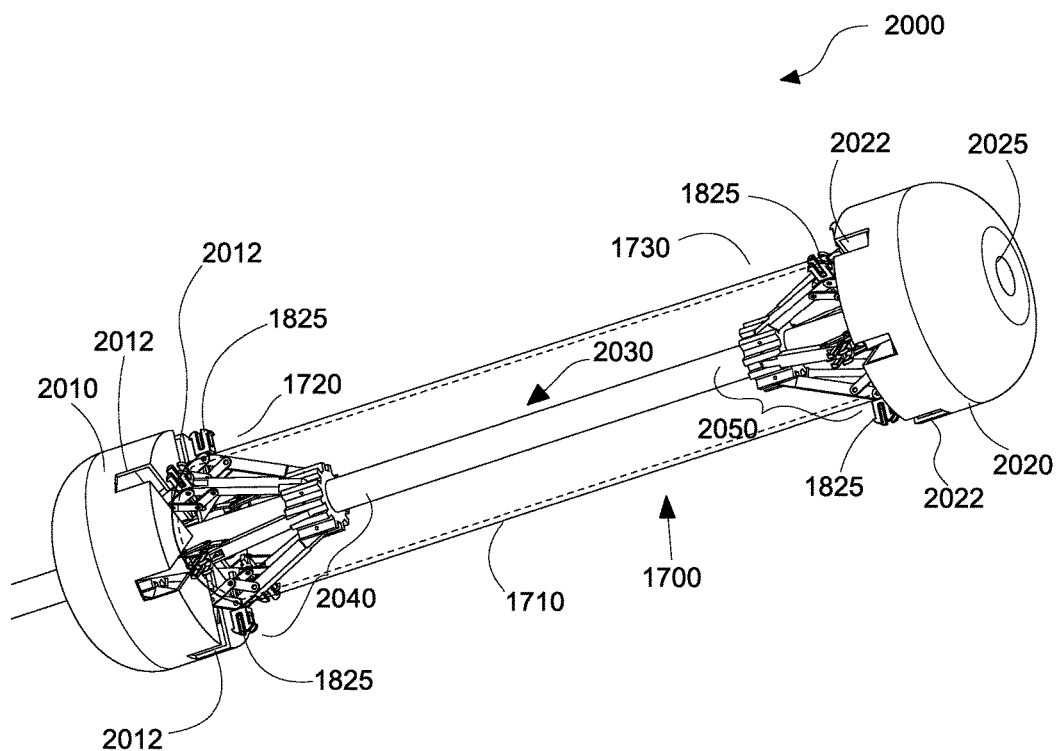
FIG. 20 illustrates the stent of FIG. 17 mounted within a stent deployment device, in an unexpanded configuration, in accordance with an embodiment of the present disclosure.

FIG. 20 illustrates the stent 1700 of FIG. 17 mounted within a stent deployment device 2000, in an unexpanded configuration, in accordance with an embodiment of the present disclosure.

The stent deployment device 2000 includes a first stent holder 2010 and a second stent holder 2020. The second stent holder 2020 includes a channel 2025 for receiving a surgical instrument therethrough. The proximal end 1720 of the stent 1700 is connected to the recesses 2012 of the first stent holder 2010 via the plurality of tacks 1825. The distal end 1730 of the stent 1700 is connected to the recesses 2022 of the second stent holder 2020 via the plurality of tacks 1825. The stent 1700 is mounted to the stent deployment device 2000 in an unexpanded configuration.

The first stent holder 2010 includes a first linkage mechanism 2040 and the second stent holder 2020 includes a second linkage mechanism 2050. The first and second linkage mechanisms 2040, 2050 are similar to each other and are described in detail below.

The linkage mechanisms 2040, 2050 axially stretch the stent 1700, and then expand and attach the proximal and distal ends 1720, 1730 of the stent 1700 to an inner wall of a lumen (not shown). The first and second stent holders 2010, 2020 may also be considered protective covers for protecting the organs when the stent deployment device 2000 is introduced or inserted or removed from the body of a patient (not shown). The linkage mechanisms 2040, 2050 are driven by the shaft 2030 connecting the first and second linkage mechanisms 2040, 2050 to each other.

Figure 21A:
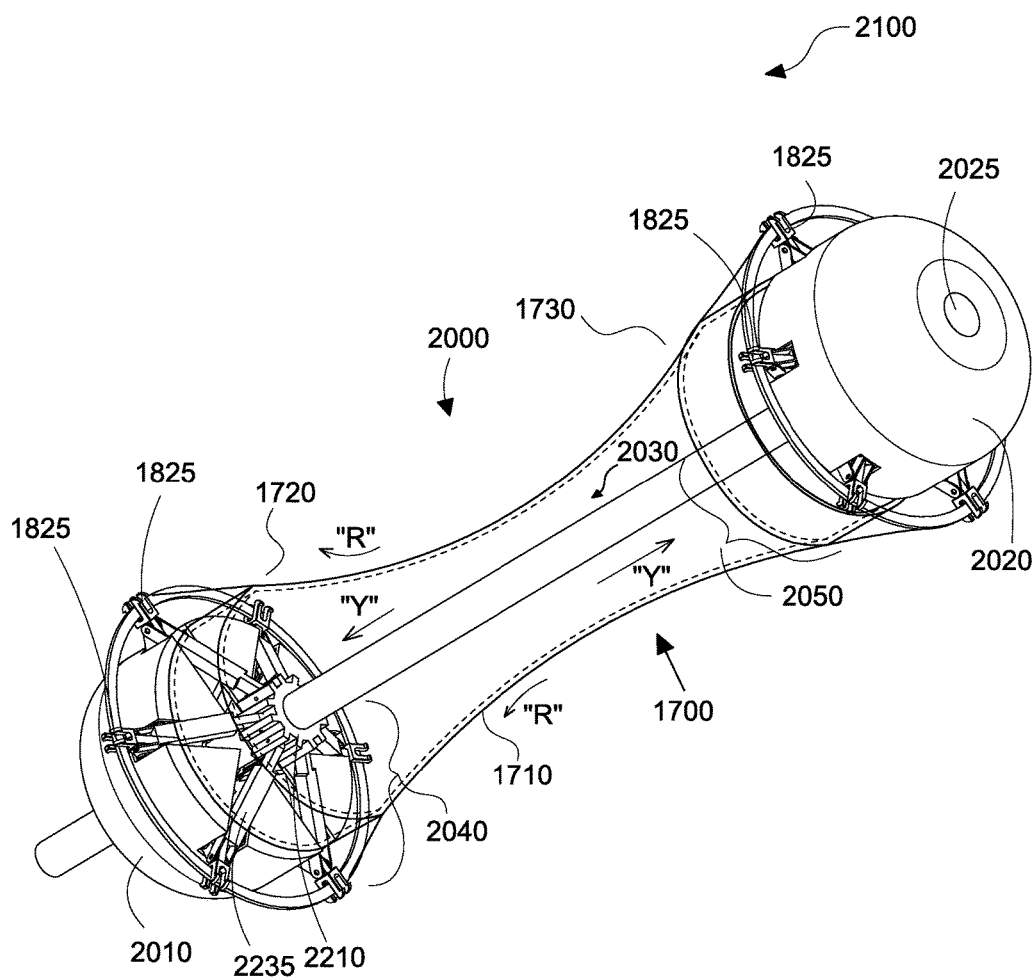
FIG. 21A illustrates the stent of FIG. 17 mounted within a stent deployment device, in an expanded configuration, in accordance with an embodiment of the present disclosure.
Figure 21B:
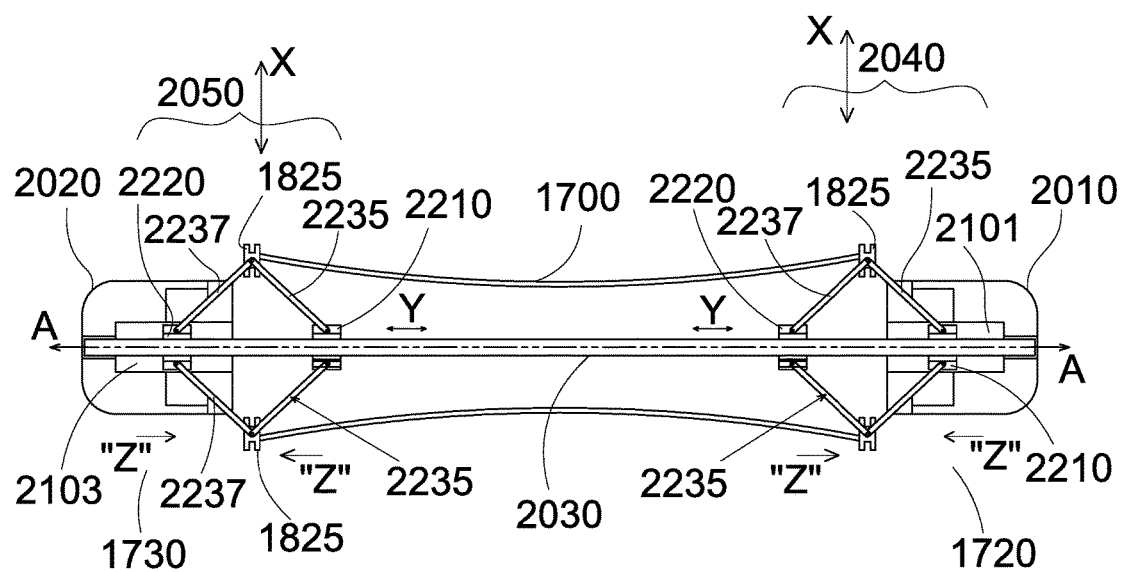
FIG. 21B illustrates a cross-sectional view of the stent deployment device of FIG. 21A, in accordance with an embodiment of the present disclosure.

FIG. 21A illustrates the stent 1700 of FIG. 17 mounted within the stent deployment device 2000 in an expanded configuration 2100, in accordance with an embodiment of the present disclosure, whereas FIG. 21B illustrates a cross-sectional view of the stent deployment device 1700, in accordance with an embodiment of the present disclosure.

Figure 22:
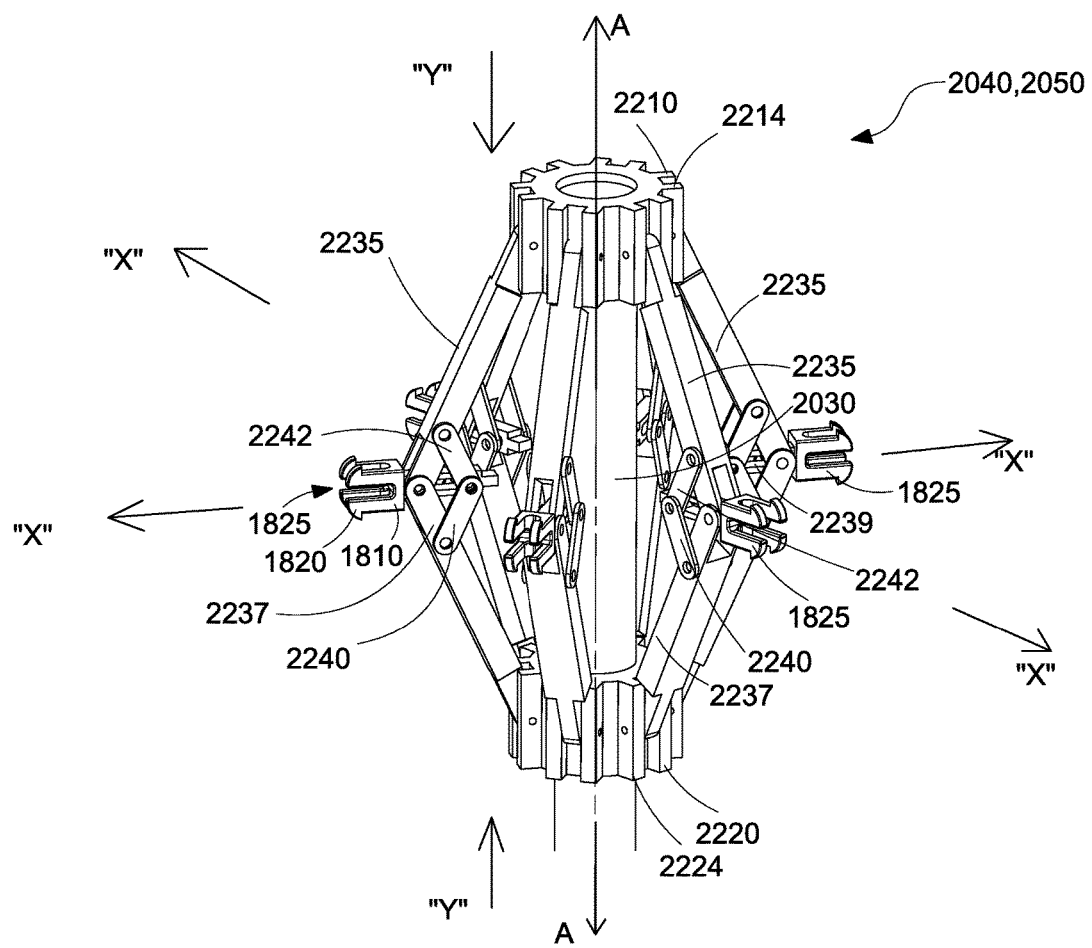
FIG. 22 illustrates a linkage mechanism for transitioning the stent of FIG. 17 from an unexpanded configuration to an expanded configuration, in accordance with an embodiment of the present disclosure.

The outer perimeter of the proximal and distal ends 1720, 1730 of the stent 1700 is held in place by the plurality of tacks 1825. In use, when the stent 1700 is expanded, the linkage mechanism 2040 is compressed such that the first and second mechanism rings 2210, 2220 (FIG. 21B) move in a direction "Y" along the shaft 2030. The first mechanism ring 2210 moves the linkage arms 2235 such that they radially expand the proximal end 1720 of the stent 1700 in a direction "R." Similarly, the second ring mechanism 2220 moves the linkage arms 2235 such that they radially expand the distal end 1730 of the stent 1700 in a direction "R" (FIG. 22). The second linkage mechanism 2050 operates in a similar manner to the first linkage mechanism 2040 in order to expand the distal end 1730 of the stent 1700.

Moreover, the axial elongation of the stent 1700 causes radial compression when the stent 1700 is being inserted into a lumen. Once the stent 1700 is anchored, removing the stent delivery system 2000 allows the stent 1700 to axially compress and radially dilate, which maintains patency and a tension free joint. This is achieved, for example, by the shape of the stent body's mesh and memory.

FIG. 22 illustrates linkage mechanisms 2040, 2050 for transitioning the stent 1700 of FIG. 17 from an unexpanded configuration to an expanded configuration, and vice versa, in accordance with an embodiment of the present disclosure.

For simplicity, the operation of the first linkage mechanism 2040 is described with reference to FIG. 22. The second linkage mechanism 2050 operates in a similar manner to the first linkage mechanism 2040. The first linkage mechanism 2040 includes the first ring mechanism 2210 and the second ring mechanism 2220. The first and second ring mechanisms 2210, 2220 are mounted on the shaft 2030. The first ring mechanism 2210 includes a plurality of teeth 2214 and the second ring mechanism 2220 includes a plurality of teeth 2224.

A plurality of links or linkages are positioned between the first and second ring mechanisms 2210, 2220. The first ring mechanism 2210 is connected to the second ring mechanism 2220 via a set of upper linkage arms 2235 and a set of lower linkage arms 2237. The upper linkage arms 2235 are pivotably coupled to the lower linkage arms 2237 via linkage members 2240, 2242. The connection points of the upper linkage arms 2235 and the lower linkage arms 2237 are configured to receive tacks 1825 via a fixed linkage 2239. The fixed linkage 2239 is substantially perpendicular to the longitudinal axis "A" defined by the shaft 2030. Each fixed linkage 2239 has a tack 1825 attached at a distal end thereof. Each tack 1825 is mounted on the first linkage mechanism 2040 such that the legs 1820 of the body portion 1810 of the tack is perpendicular to the first and second ring mechanisms 2210, 2220.

In use, when the stent 1700 is expanded, the link mechanism 2040 is compressed such that the first and second mechanism rings 2210, 2220 of the first linkage mechanism 2040 move in a direction "Y" along the shaft 2030. Thus, the first and second mechanism rings 2210, 2220 move closer together along the shaft 2030. This results in the upper and lower linkage arms 2235, 2237 moving in a direction "X" away from a longitudinal axis "A" defined by the shaft 2030. This results in the tacks 1825 also moving in a direction "X." The tacks 1825 are configured to be inserted into a distal end of the fixed linkage 2239.

FIG. 21B depicts how the first linkage mechanism 2040 and the second linkage mechanism 2050 are mounted on the shaft 2030. The first linkage mechanism 2040 is positioned on the proximal end 1720 of the shaft 2030, whereas the second linkage mechanism 2050 is positioned on the distal end 1730 of the shaft 2030. The first and second ring mechanisms 2210 and 2220 of the first linkage mechanism 2040 are shown in a compressed configuration such that the stent 1700 is in an expanded state. Similarly, the first and second ring mechanisms 2210 and 2220 of the second linkage mechanism 2050 are shown in a compressed configuration such that the stent 1700 is in an expanded state. The first ring mechanism 2210 of the first linkage mechanism 2040 moves within recess 2101 in a direction "Y," whereas the second ring mechanism 2220 of the second linkage mechanism 2050 moves within recess 2103 in a direction "Y." The upper and lower linkage arms 2235, 2237 move in a direction "Z" when the stent 1700 is transitioned into the expanded configuration of FIGS. 21A, 21B. This results in the tacks 1825 extending outwardly in the "X" direction. Thus, the tacks 1825 move perpendicular to the axis "A" defined by the shaft 2030. Thus, the first and second mechanism rings 2210, 2220 aid in radially expanding the stent 1700.

In summary, the stent deployment device 2000 uses two independent linkage mechanisms 2040, 2050 to axially stretch the stent 1700, and then expand and attach distal and proximal segments of the stent 1700 to the inner walls of a lumen. The two protective covers 2010, 2020 protect the organs when the stent deployment device 2000 is inserted or removed from the body of a patient. The linkage mechanisms 2040, 2050 may be driven by a series of concentric and hollow tubes (or by central tube or shaft 2030) connected to the first and second ring mechanisms 2210, 2220. The central tube or shaft 2030 may house the scope, a guide wire or additional instrumentation. The stent 1700 may have fasteners or anchors or tacks 1825 radially placed around the edges of the stent 1700. The tacks 1825 may be temporarily or permanently attached thereto. The fasteners 1825 may also have openings for placement on the fixed linkage 2239 connecting the first and second (or upper and lower) linkage arms 2235, 2237. When the first and second ring mechanisms 2210, 2220 travel along the shaft 2030, the tacks 1825 move radially inward or radially outward, thus adjusting the radial position of the stent 1700 when placed with the lumen.

Figure 23A:
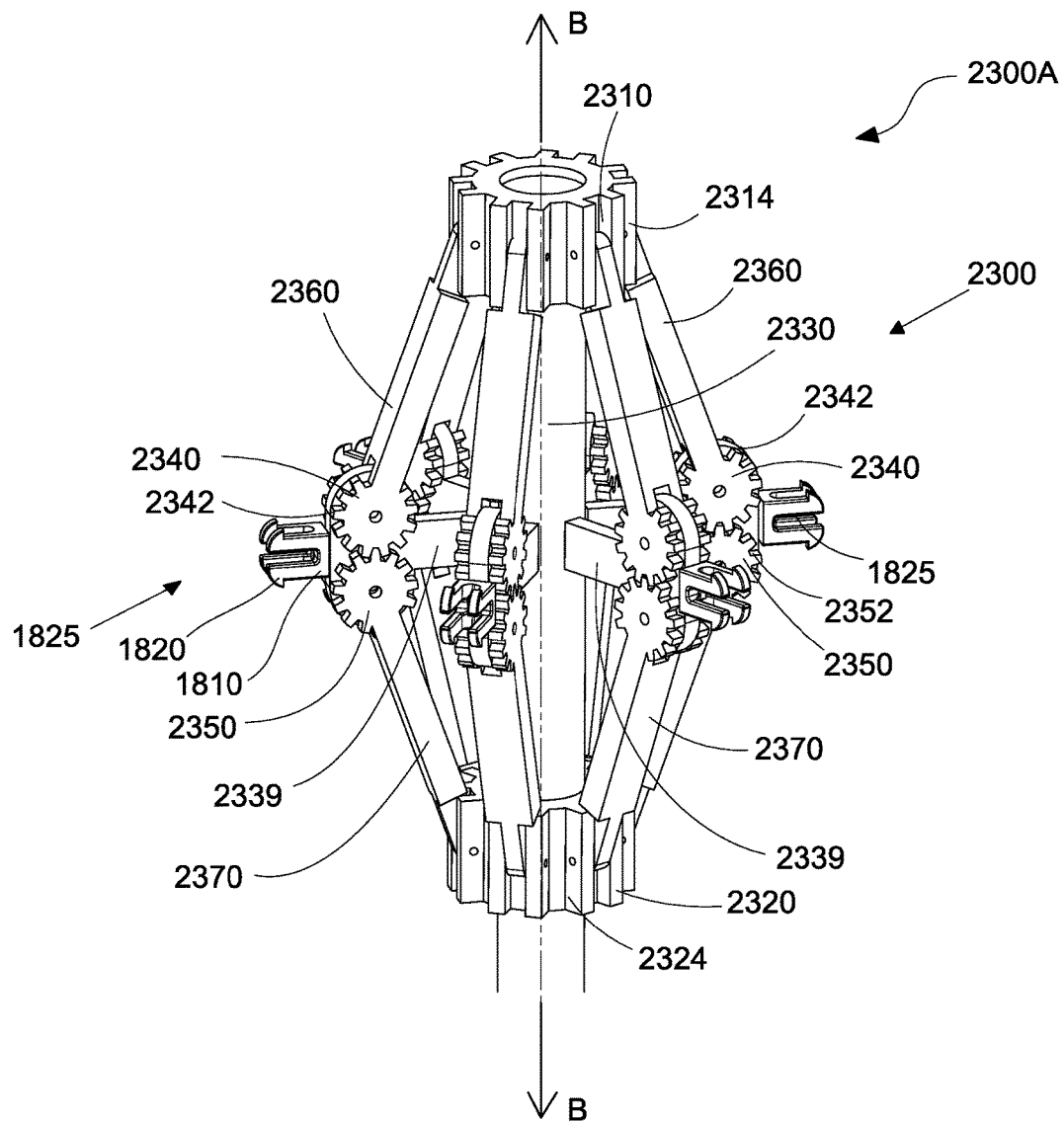
FIGS. 23A and 23B illustrate a linkage mechanism transitioning from a first configuration to a second configuration, in accordance with another embodiment of the present disclosure.
Figure 23B:
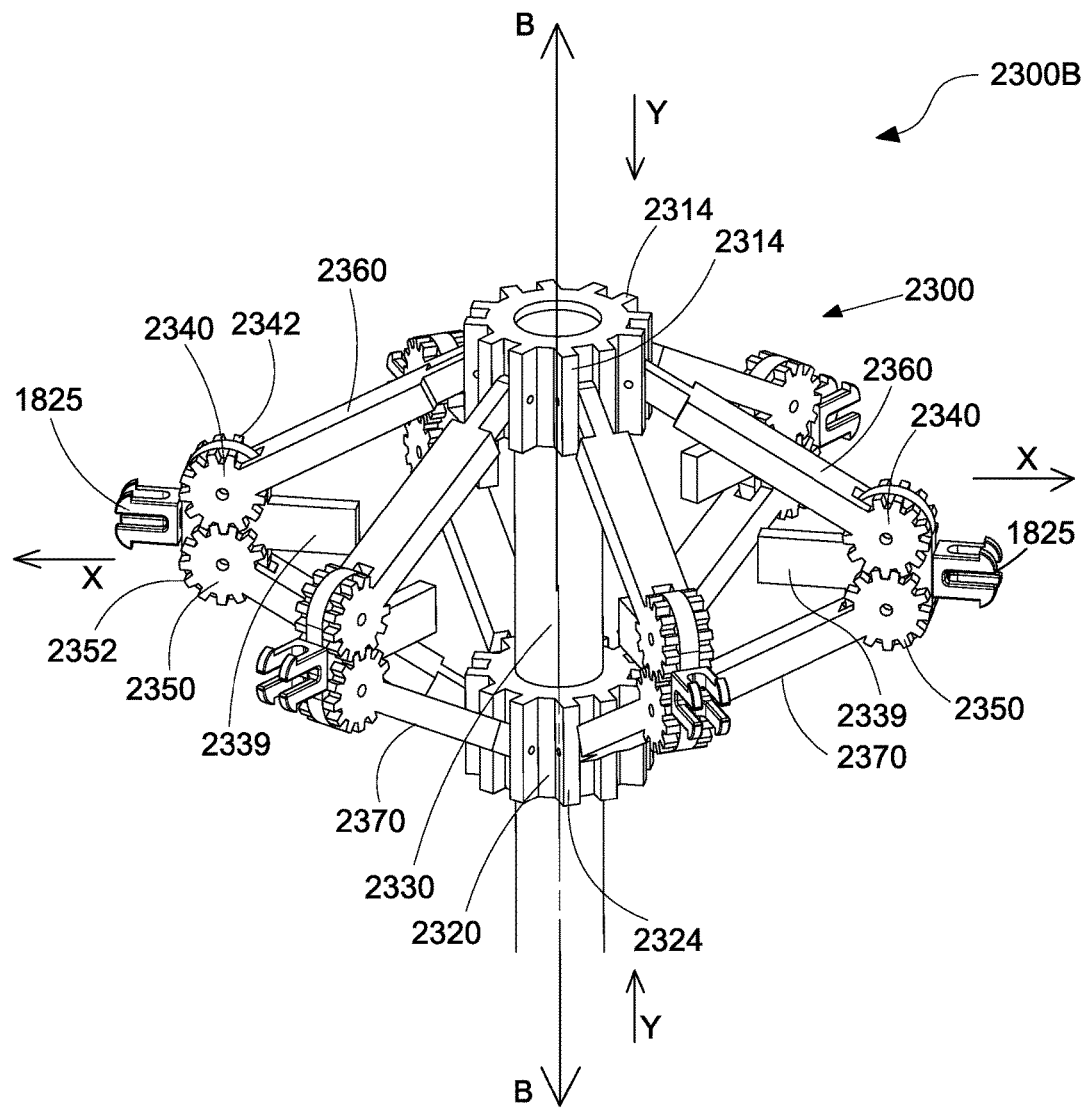

FIGS. 23A and 23B illustrate a linkage mechanism 2300 transitioning from a first configuration 2300A to a second configuration 2300B, in accordance with another embodiment of the present disclosure.

In an alternative embodiment, FIG. 23A illustrates an unexpanded configuration 2300A of the linkage mechanism 2300, whereas FIG. 23B illustrates an expanded configuration 2300B of the linkage mechanism 2300.

The linkage mechanism 2300 includes a first ring mechanism 2310 and a second ring mechanism 2320. The first and second ring mechanisms 2310, 2320 are mounted on the shaft 2330. The first ring mechanism 2310 includes a plurality of teeth 2314 and the second ring mechanism 2320 includes a plurality of teeth 2324.

A plurality of links or linkages are positioned between the first and second ring mechanisms 2310, 2320. The first ring mechanism 2310 is connected to the second ring mechanism 2320 via a set of upper linkage arms 2360 and a set of lower linkage arms 2370. The upper linkage arms 2360 are pivotably connected or coupled to the lower linkage arms 2370 via linkage members 2340, 2350. Linkage members 2340 include teeth 2342 and linkage members 2350 include teeth 2352. The connection points of the upper linkage arms 2360 and the lower linkage arms 2370 are configured to receive tacks 1825 via a fixed linkage 2339. Each tack 1825 is mounted on the linkage mechanism 2300 such that the legs 1820 of the body portion 1810 of the tack 1825 is perpendicular to the first and second ring mechanisms 2310, 2320. Thus, the first and second mechanism rings 2210, 2220 aid in radially expanding the stent 1700.

In use, when the stent 1700 is expanded, the link mechanism 2300 is compressed such that the first and second mechanism rings 2310, 2320 of the link mechanism 2300 moves in a direction "Y" along the shaft 2330. Thus, the first and second mechanism rings 2310, 2320 move closer together along the shaft 2330. This results in the upper and lower linkage arms 2335, 2337 moving in a direction "X" away from a longitudinal axis "B" defined by the shaft 2330. This further results in the tacks 1825 also moving in a direction "X." The tacks 1825 are configured to be inserted into a distal end of a plurality of fixed linkage 2339.

Figure 24:
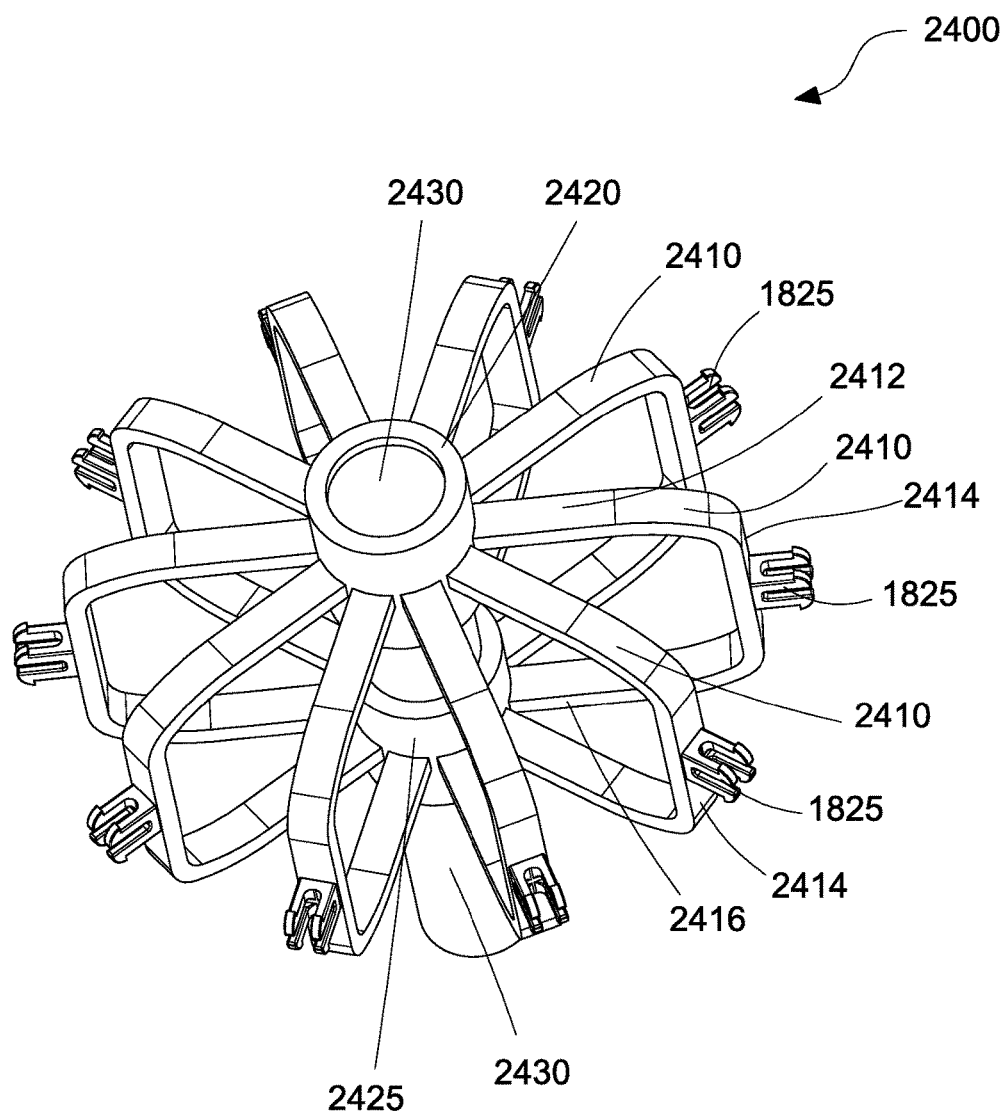
FIG. 24 illustrates another embodiment of a linkage mechanism for transitioning the stent of FIG. 17 from an unexpanded configuration to an expanded configuration, in accordance with an embodiment of the present disclosure.

FIG. 24 illustrates another embodiment of a linkage mechanism 2400 for transitioning the stent 1700 of FIG. 17 from an unexpanded configuration 2400A to an expanded configuration 2400B, in accordance with an embodiment of the present disclosure.

The linkage mechanism 2400 includes linkage arms 2410 that extend between the first ring mechanism 2420 and the second ring mechanism 2425. The first and second ring mechanisms 2420, 2425 are mounted on the shaft 2430 of the linkage mechanism 2400. The tacks 1825 are mounted on a central portion 2414 of the linkage arms 2410. Each linkage arm 2410 may include a first portion 2412 and a second portion 2416 connected to each other via the central portion 2414. Each linkage arm 2410 defines a continuous surface extending from the first ring mechanism 2420 to the second ring mechanism 2425. The linkages 2410 may be equally spaced apart from each other in a circumferential manner. The linkage arm 2400 operates in a similar manner to the first and second linkage mechanisms 2040, 2050 of FIGS. 20-22.

Figure 25:
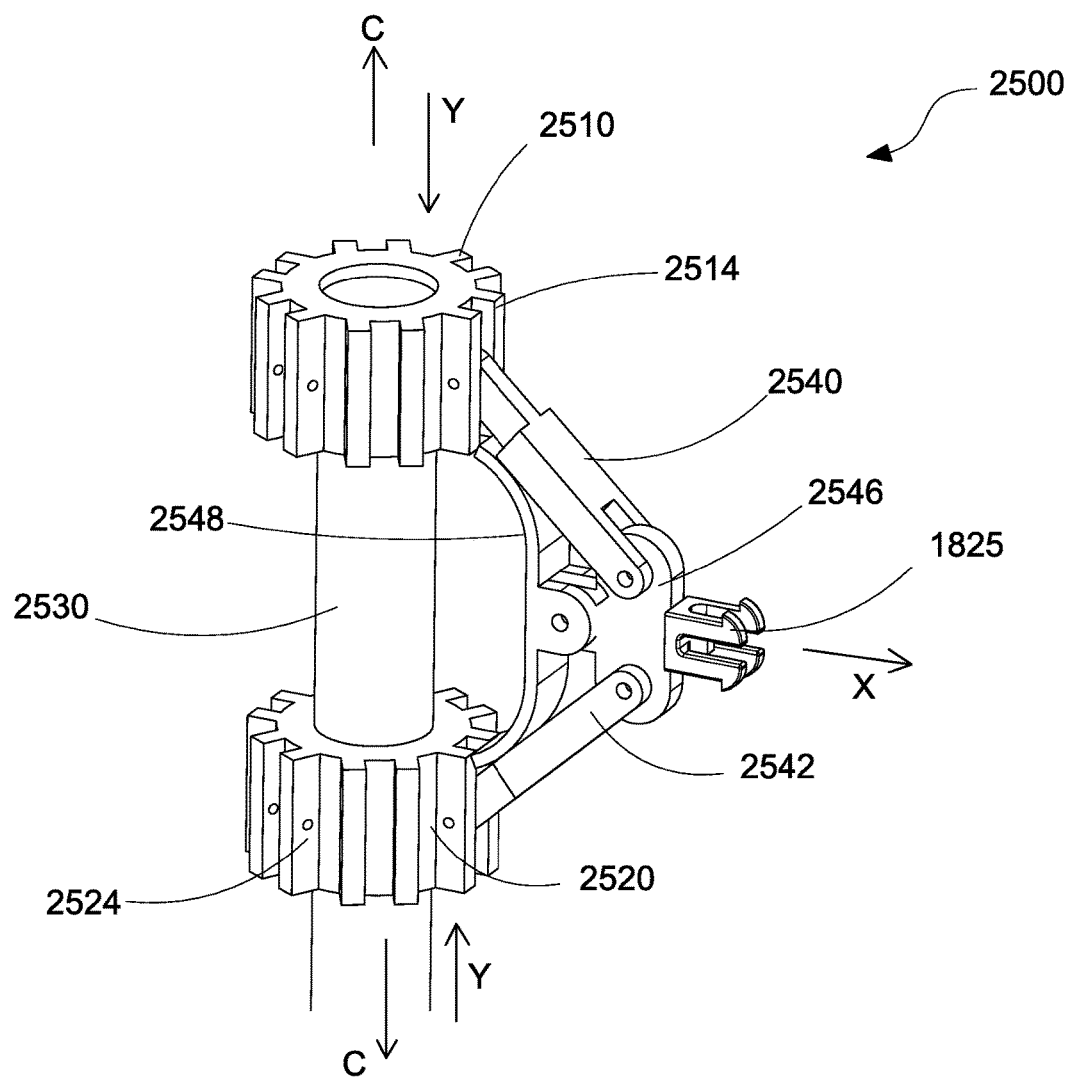
FIG. 25 illustrates another embodiment of a linkage mechanism for transitioning the stent of FIG. 17 from an unexpanded configuration to an expanded configuration, in accordance with an embodiment of the present disclosure.
Figure 26:
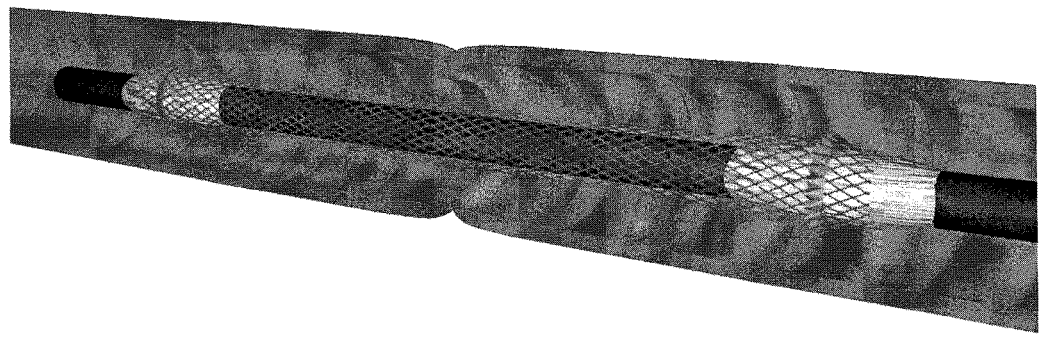
FIG. 26 is another embodiment of an introducer placed over an anastomosis, in accordance with an embodiment of the present disclosure.
Figure 27:
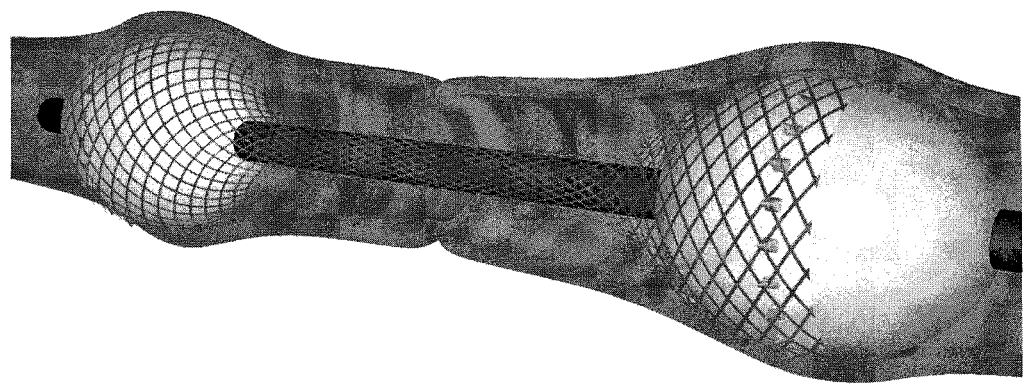
FIG. 27 illustrates the deployment of the stent of FIG. 26 with a pair of balloons, in accordance with an embodiment of the present disclosure.
Figure 28:
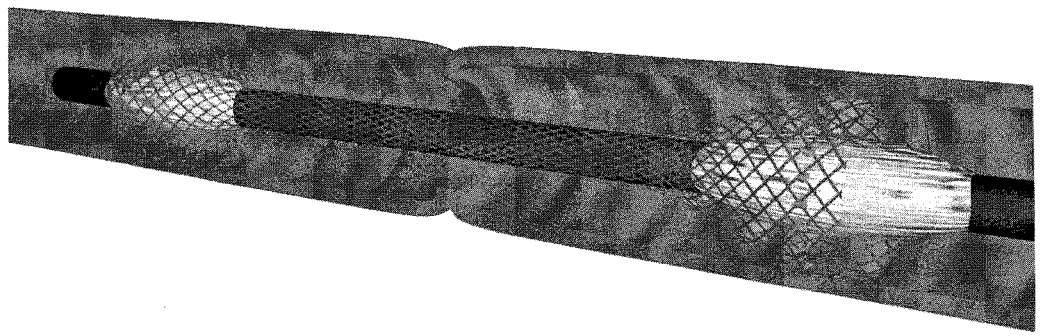
FIG. 28 illustrates the balloons of FIG. 27 being deflated, in accordance with an embodiment of the present disclosure.
Figure 29:
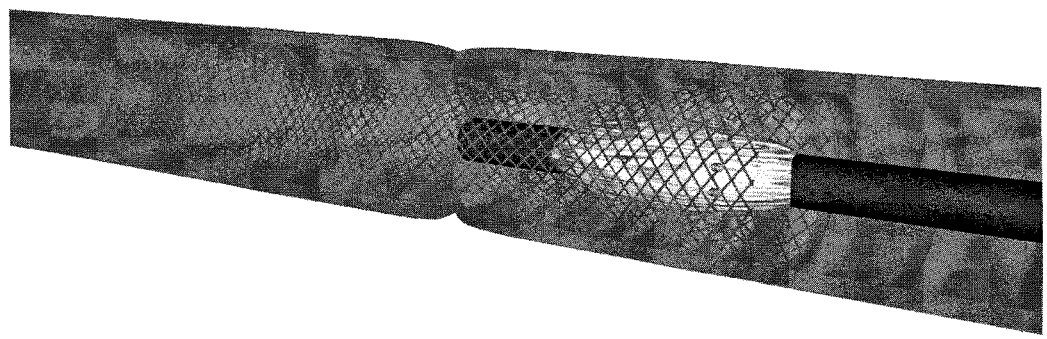
FIG. 29 illustrates the introducer of FIG. 26 being removed from the anastomosis site, in accordance with an embodiment of the present disclosure.
Figure 30:
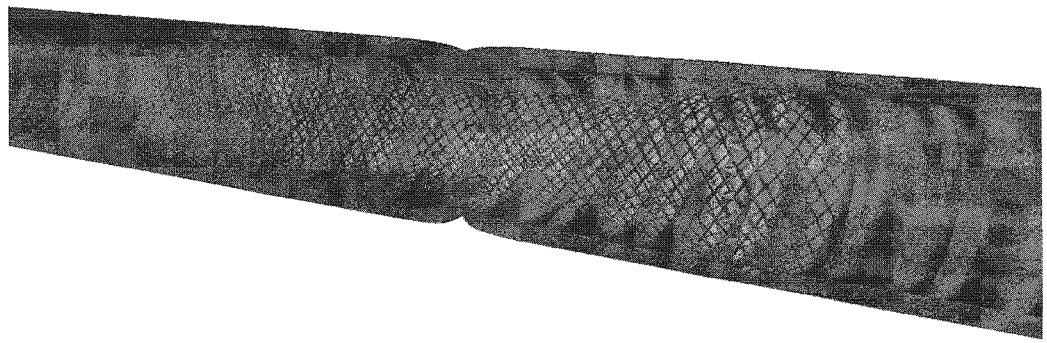
FIG. 30 illustrates the stent of FIG. 26 held in place at the anastomosis site, in accordance with an embodiment of the present disclosure.
Figure 31:
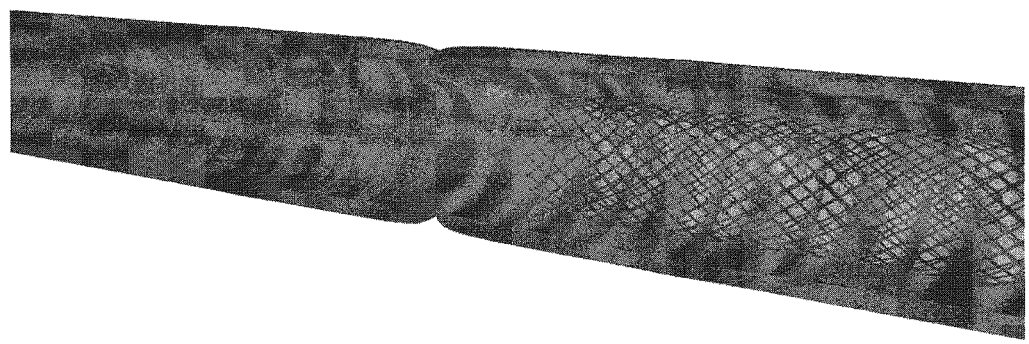
FIG. 31 illustrates the stent of FIG. 30 being removed from the anastomosis site, in accordance with an embodiment of the present disclosure.
Figure 32:
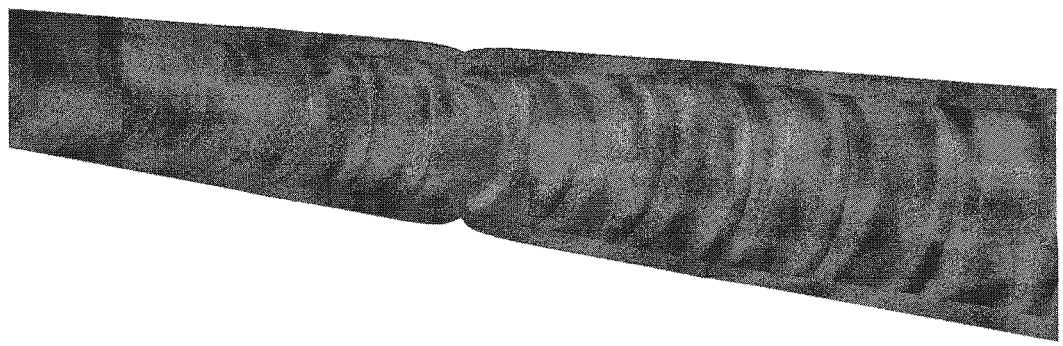
FIG. 32 illustrates the anastomosis being fully healed, in accordance with an embodiment of the present disclosure.

FIG. 25 illustrates another embodiment of a linkage mechanism 2500 for transitioning the stent 1700 of FIG. 17 from an unexpanded configuration 2500A to an expanded configuration 2500B, in accordance with an embodiment of the present disclosure.

The linkage mechanism 2500 includes a first ring mechanism 2510 and a second link mechanism 2520. The first ring mechanism 2510 includes a plurality of teeth 2514 and the second ring mechanism 2520 includes a plurality of teeth 2524. The first and second ring mechanisms 2510, 2520 are mounted on a shaft 2530. The first and second ring mechanisms 2510, 2520 are connected to each other via a first link arm 2540 and a second link arm 2542. The first and second link arms 2540, 2542 are connected to each other via a link member 2546. The link member 2546 further includes a stabilizing component 2548 for stabilizing the first link arm 2540 to the second link arm 2542. The stabilizing component 2548 is secured between the teeth 2514 of the first ring mechanism 2510 and the teeth 2524 of the second ring mechanism 2520. The tacks 1825 are connected to the distal end of the link member 2546.

In a compressed configuration, the first and second ring mechanisms 2510, 2520 move in a direction "Y" and the first and second link arms 2540, 2542 move in a direction "X" along with the tack 1825. Thus, the tack 1825 moves perpendicular to the longitudinal axis "C" defined by the shaft 2530. The linkage arm 2500 operates in a similar manner to first and second linkage mechanisms 2040, 2050 of FIGS. 20-22.

FIGS. 26-33 depict another embodiment of a stent deployment device, in accordance with aspects of the present disclosure.

The stent shown in FIGS. 26-30 has a tubular shape and stretches axially and radially. The fasteners are permanently attached to the stent. Two "rings" of the fasteners are located at the openings of the stent (see FIG. 26). The introducer includes a hollow shaft and two deployment balloons (see FIG. 27). The stent is placed over the introducer in such a way that the rings of the fasteners are aligned with deployment balloons. The user may insert the introducer into the lumen and align central parts of the stent with the anastomotic site (see FIG. 26). The user may inflate the balloons, which expand and radially stretch the stent at the edges until the fasteners engage luminal walls (see FIG. 27). The user then deflates the balloons and removes the introducer from the lumen (see FIGS. 28-29), thus leaving the stent in place (see FIG. 30). When the healing is completed, the absorbable fasteners disintegrate and the stent is expelled from the body, thus leaving healed hollow organ behind (see FIGS. 31-32).

Figure 33:
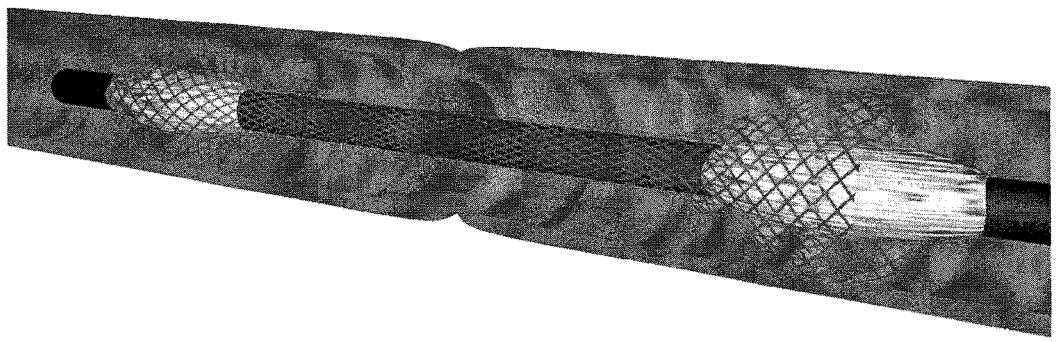
FIG. 33 illustrates another embodiment where barbed sutures are used to aid in the shortening of a stent to release the tension at the anastomosis site, in accordance with an embodiment of the present disclosure.

In the embodiment shown in FIG. 33, the barbed sutures are intertwined with the stent mesh. After deployment, the user can pull sutures proximally, which will contract the stent axially and lock it in this state by suture barbs engaging the mesh. The shortened stent relieves tension over anastomosis area and helps prevent leaks. The advantages of FIGS. 26-33 include at least (1) that the mechanism is simple and allows controlled attachment of both ends of the stent to the lumen wall, (2) a hollow central shaft that can accept auxiliary instrumentation (scope, grasper, etc.) and (3) the barbed suture based tightening mechanism allows for the release of tension in the anastomotic area and thus prevent leaks.

In all the embodiments described above, the stent deployment devices may include lighting means, such as light emitting diodes (LEDs). The LEDs may enable the guided positioning of the stent deployment devices, as well as guided positioning of the proximal and distal ends of the stent. The LEDs may also enable identification of the location of the anastomosis. The LEDs may be sufficiently bright to be viewed through the wall of the hollow structures in which they are placed.

The advantages of the present disclosure are that a stent is deployed intraluminally in the GI tract after completion of an end-to-end anastomosis so that the most distant segment is distal to the anastomosis, the central segment overlaps the anastomosis, and the nearest segment is proximal to the anastomosis. The impermeable lining material of the stent may include anti-bacterial coating to further promote healing of the anastomosis. The stent deployment devices enable deployment of the stent within an end-to-end anastomosis area intraluminally with minimal invasiveness. Additionally, the stent deployment devices provide a means of axially stretching the stent and attaching it to the wall of a lumen in a stretched or axially expanded state. As a result, once the stent deployment device is separated from the stent, the stent contracts axially, thus reducing tension applied to the staple line or anastomosis. This further promotes healing and minimizes the risk of leaks.

Further advantages of the present disclosure are that the stent deployment devices can expand proximal and distal segments of the stents to a desired radius independently of each other, and, thus, adjust to the varying diameter of the organ. In one exemplary embodiment, the plurality of fasteners (anchors) attaching the stent to the wall of the lumen are radially deployed (piercing the tissue) ensuring a strong circumferential luminal seal. In another embodiment, the stent deployment device has a flexible shaft that helps to pass the stent deployment device through tortuous paths. The stent deployment devices may have a working channel for a guide wire, grasper or flexible scope to ensure visualization of the surgical site.

While the stent/implant device in the exemplary embodiments presented herein may be used within the esophagus, stomach, colon/rectum and anus, it is understood that these are exemplary embodiments presented to demonstrate aspects of the present disclosure. The description provided herein may refer to the deployment of a stent/implant device in particular to the esophagus, stomach, colon and rectum, but it is also understood that aspects of the present disclosure may be employed within other part of the gastrointestinal tract such as the small intestine and biliary tract.

The impermeable membranes described herein may be impermeable to, among other things, alimentary tract content such as, for example, bile, water, and/or fecal matter. Further, although the membranes may be described as having at least portions that are not directly radially supported, it should be understood that an underlying support, e.g., a stent structure may be provided along at least one or more portions of the membranes.

It is to be understood that the various embodiments shown and described herein are to be taken as exemplary. Elements and materials, and arrangements of those elements and materials, may be substituted for those illustrated and described herein, parts may be reversed, and certain features of the present disclosure may be utilized independently, all as would be apparent to one skilled in the art after having the benefit of the description herein. Changes may be made in the elements described herein without departing from the spirit and scope of the present disclosure and following claims, including their equivalents. It is to be understood that the particular examples and embodiments set forth herein are non-limiting, and modifications to structure, dimensions, materials, and methodologies may be made without departing from the scope of the present disclosure.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

The invention claimed is:

1. A stent deployment system, comprising:
a handle body;
a stent holding assembly including a first holder and a second holder, the stent holding assembly connected to the handle body, wherein the first holder is connected to the second holder via a shaft defining a longitudinal axis such that the first and second holders are substantially aligned with the longitudinal axis;
a stent having a proximal end and a distal end, the stent secured to the stent holding assembly such that at least a portion of the stent holding assembly is confined within the stent;
a first protective cover disposed at one end of the first holder, the first protective cover configured to enclose a first fastening assembly; and
a second protective cover disposed at one end of the second holder, the second protective cover configured to enclose a second fastening assembly, each of the first and second fastening assemblies including a plurality of anchors, wherein the plurality of anchors are movable from a straight configuration when enclosed by the respective first and second protective covers to a bent configuration when the plurality of anchors are released from the respective first and second protective covers.

2. The stent deployment system according to claim 1, wherein each of the first and second fastening assemblies includes extensions, the plurality of anchors mounted on distal ends of the extensions, the extensions separated from each other by gaps.

3. The stent deployment system according to claim 2, wherein the first and second fastening assemblies are exposed upon removal of the first and second protective covers, respectively.

4. The stent deployment system according to claim 3, wherein the first holder includes a first sleeve and the second holder includes a second sleeve, the first and second sleeves removed before deployment of the first and second fastening assemblies.

5. The stent deployment system according to claim 4, wherein, upon removal of the first and second sleeves, the extensions of each of the first and second fastening assemblies are actuated to extend away from the first and second holders to engage a lumen.

6. The stent deployment system according to claim 5, wherein the stent is positioned within the lumen in an axially expanded configuration.

7. The stent deployment system according to claim 6, wherein, when the first and second fastening assemblies are actuated to extend away from the first and second holders, the stent secured thereon deforms to a radially expanded configuration.

8. The stent deployment system according to claim 1, wherein the first and second holders are independently driven.

9. The stent deployment system according to claim 1, wherein each of the first and second holders is a substantially cylindrical enclosure, where the respective first and second fastening assemblies are circumferentially positioned therein.

* * * * *